(12) United States Patent
Inoue et al.

(10) Patent No.: US 9,186,056 B2
(45) Date of Patent: Nov. 17, 2015

(54) DEVICE AND METHOD FOR DETERMINING CONVERGENCE EYE MOVEMENT PERFORMANCE OF A USER WHEN VIEWING A STEREOSCOPIC VIDEO

(71) Applicant: Panasonic Intellectual Property Management Co., Ltd., Osaka (JP)

(72) Inventors: Tsuyoshi Inoue, Nara (JP); Jun Ozawa, Nara (JP); Yumiko Kato, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 13/627,491

(22) Filed: Sep. 26, 2012

(65) Prior Publication Data

US 2013/0021456 A1   Jan. 24, 2013

Related U.S. Application Data

(63) Continuation of application No. PCT/JP2012/002345, filed on Apr. 4, 2012.

(30) Foreign Application Priority Data

May 19, 2011   (JP) .................. 2011-112680

(51) Int. Cl.
  *H04N 13/04*   (2006.01)
  *A61B 3/10*   (2006.01)
  *H04N 13/00*   (2006.01)
  *G06F 3/01*   (2006.01)
(52) U.S. Cl.
  CPC .............. *A61B 3/10* (2013.01); *H04N 13/0033* (2013.01); *H04N 13/0468* (2013.01); *G06F 3/013* (2013.01); *H04N 2213/002* (2013.01)

(58) Field of Classification Search
  CPC combination set(s) only.
  See application file for complete search history.

(56) References Cited

U.S. PATENT DOCUMENTS

| | | | | |
|---|---|---|---|---|
| 5,561,537 A | * | 10/1996 | Aritake et al. | 359/23 |
| 6,671,391 B1 | * | 12/2003 | Zhang et al. | 382/118 |
| 8,760,502 B2 | * | 6/2014 | Yoon et al. | 348/49 |

(Continued)

FOREIGN PATENT DOCUMENTS

| | | |
|---|---|---|
| JP | 9-18894 | 1/1997 |
| JP | 2004-333661 | 11/2004 |

(Continued)

OTHER PUBLICATIONS

Yuji Nojiri ; Hirokazu Yamanoue ; Atsuo Hanazato ; Masaki Emoto ; Fumio Okano, "Visual comfort/discomfort and visual fatigue caused by stereoscopic HDTV viewing" Proc. SPIE 5291, Stereoscopic Displays and Virtual Reality Systems XI, 303 (May 21, 2004).*

(Continued)

*Primary Examiner* — Dave Czekaj
*Assistant Examiner* — Tyler W Sullivan
(74) *Attorney, Agent, or Firm* — Wenderoth, Lind & Ponack, L.L.P.

(57) ABSTRACT

Provided is a convergence performance determination device that determines convergence eye movement performance of a user when viewing a stereoscopic video by comparing amounts of convergence information calculated from eye information obtained from the user to predetermined amounts of convergence information. The convergence performance determination device then allows a degree of stereoscopy of the stereoscopic video being viewed by the user to be changed to a degree suitable to the user based on the determined convergence eye movement performance of the user.

8 Claims, 29 Drawing Sheets

(56) References Cited

U.S. PATENT DOCUMENTS

| | | |
|---|---|---|
| 2004/0056824 A1* | 3/2004 | Sudo et al. .................... 345/7 |
| 2006/0215111 A1* | 9/2006 | Mihashi .................... 351/205 |
| 2009/0102915 A1* | 4/2009 | Arsenich .................... 348/53 |
| 2011/0063421 A1 | 3/2011 | Kubota |
| 2011/0142309 A1* | 6/2011 | Zhang et al. .................... 382/128 |
| 2011/0172556 A1* | 7/2011 | Jones et al. .................... 600/558 |
| 2011/0228051 A1* | 9/2011 | Dedeoglu et al. .................... 348/46 |
| 2011/0267442 A1 | 11/2011 | Imai et al. |
| 2013/0021458 A1* | 1/2013 | Inoue et al. .................... 348/56 |
| 2013/0147797 A1* | 6/2013 | Tanaka .................... 345/419 |

FOREIGN PATENT DOCUMENTS

| | | |
|---|---|---|
| JP | 2010-259006 | 11/2010 |
| JP | 2011-64894 | 3/2011 |
| JP | 2011-520398 | 7/2011 |
| WO | 2009/139740 | 11/2009 |
| WO | 2010/084849 | 7/2010 |

OTHER PUBLICATIONS

International Search Report issued May 1, 2012 in International Application No. PCT/JP2012/002345.

* cited by examiner

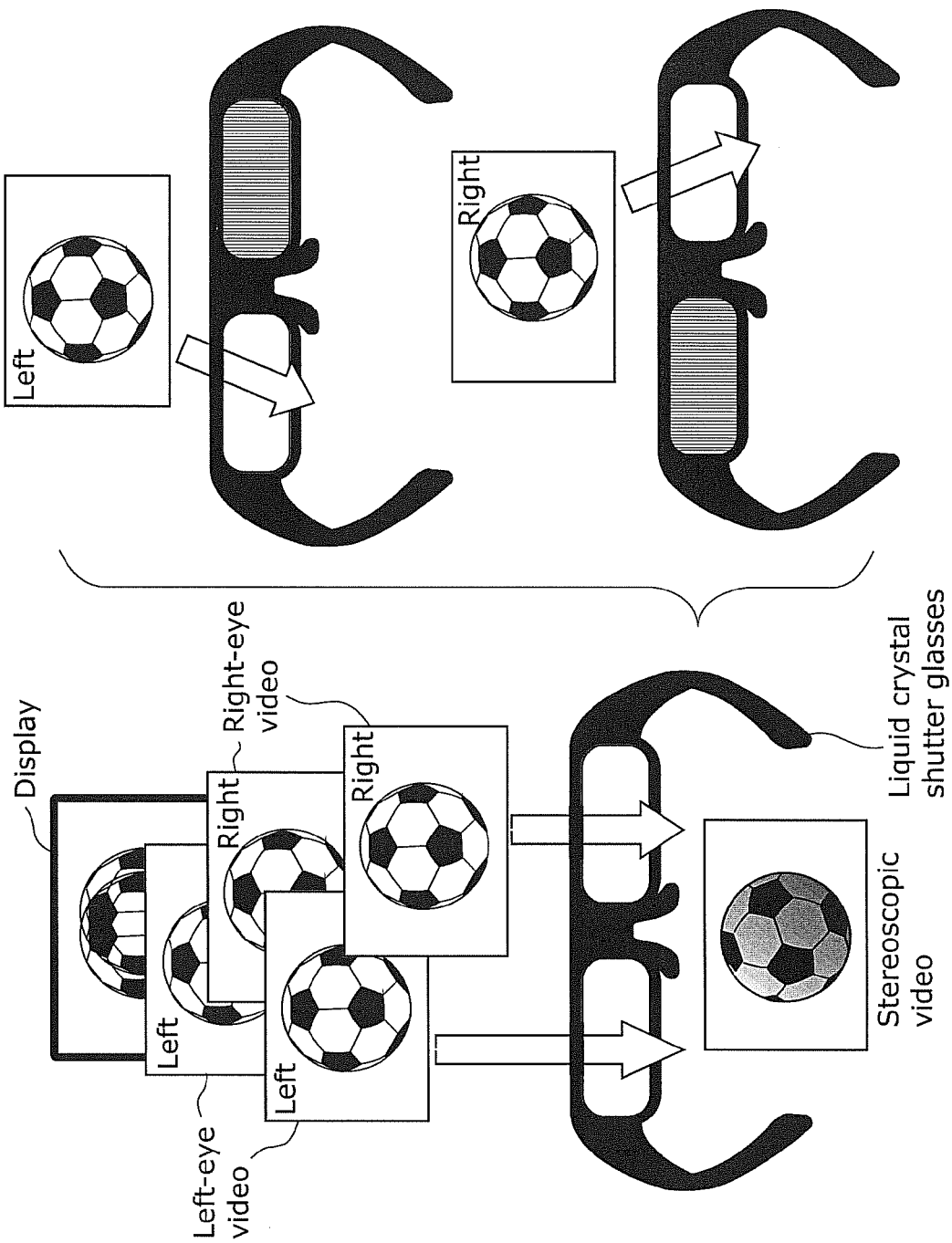

FIG. 7

| Date and time of measurement | x coordinate of right eye | x coordinate of left eye | Amount of convergence |
|---|---|---|---|
| 2010 Aug 3  19:00:10:01 | 566.91 | 190.04 | 376.87 |
| 2010 Aug 3  19:00:10:02 | 567.07 | 189.90 | 377.17 |
| 2010 Aug 3  19:00:10:03 | 567.02 | 189.83 | 377.19 |
| 2010 Aug 3  19:00:10:04 | 567.04 | 190.04 | 377.00 |
| 2010 Aug 3  19:00:10:05 | 566.99 | 189.66 | 377.33 |
| 2010 Aug 3  19:00:10:06 | 567.65 | 190.00 | 377.65 |
| 2010 Aug 3  19:00:10:07 | 567.14 | 189.44 | 377.70 |
| 2010 Aug 3  19:00:10:08 | 567.56 | 189.85 | 377.71 |
| 2010 Aug 3  19:00:10:09 | 567.16 | 189.86 | 377.31 |
| 2010 Aug 3  19:00:10:10 | 567.78 | 189.93 | 377.86 |
| 2010 Aug 3  19:00:10:11 | 567.18 | 189.64 | 377.54 |
| ... | ... | ... | ... |

701 702 703 704

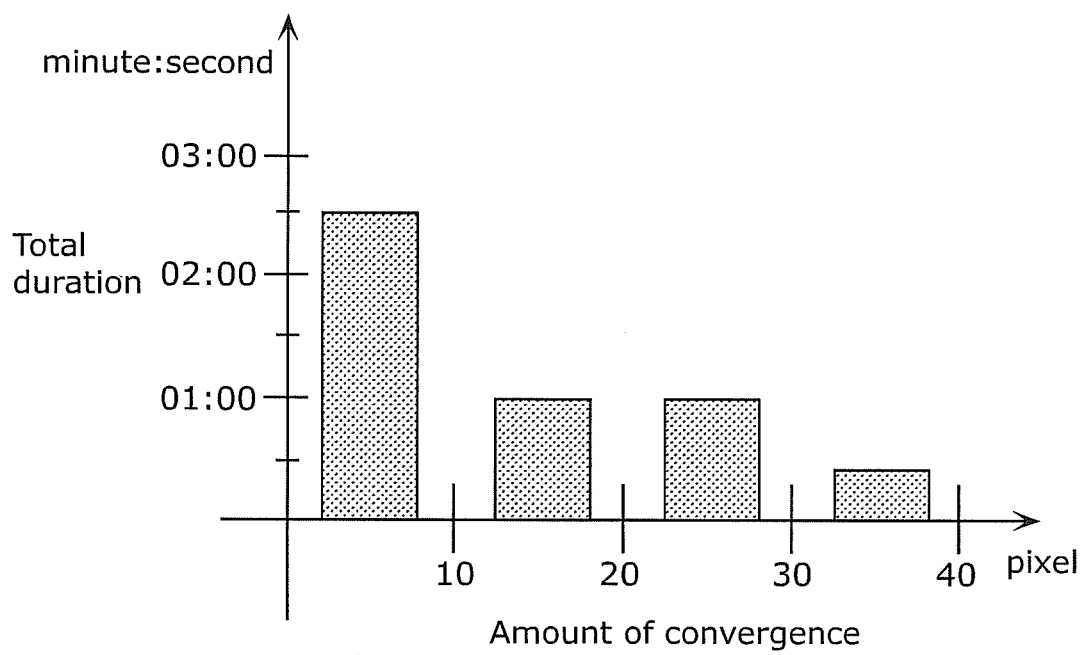

FIG. 14

| Date and time of measurement | x coordinate of right eye | x coordinate of left eye | Amount of convergence | Elapsed time |
|---|---|---|---|---|
| 2010 Aug 3  19:00:10:01 | 566.91 | 190.04 | 1.87 | -1 |
| 2010 Aug 3  19:00:10:02 | 567.07 | 189.90 | 2.17 | -1 |
| 2010 Aug 3  19:00:10:03 | 567.02 | 189.83 | 2.19 | -1 |
| 2010 Aug 3  19:00:10:04 | 567.04 | 190.04 | 2.00 | -1 |
| 2010 Aug 3  19:00:10:05 | 566.99 | 189.66 | 2.33 | -1 |
| 2010 Aug 3  19:00:10:06 | 567.65 | 190.00 | 2.65 | 00:00:00 |
| 2010 Aug 3  19:00:10:07 | 567.14 | 189.44 | 2.70 | 00:00:01 |
| 2010 Aug 3  19:00:10:08 | 567.56 | 189.85 | 2.71 | 00:00:02 |
| 2010 Aug 3  19:00:10:09 | 567.16 | 189.86 | 2.31 | 00:00:03 |
| 2010 Aug 3  19:00:10:10 | 567.78 | 189.93 | 2.86 | 00:00:04 |
| 2010 Aug 3  19:00:10:11 | 567.18 | 189.64 | 2.54 | 00:00:05 |
| ... | ... | ... | ... | ... |

1801   1802   1803   1804   1805

| ID | Degree of stereoscopy | Evaluation interval No. | Measured convergence amount distribution ||||
|---|---|---|---|---|---|---|
| | | | 0 - 10 | 10 - 20 | 20 - 30 | 30 - 40 |
| 1 | 3 | 1 | 02:30 | 01:00 | 01:00 | 00:30 |
| | | 2 | | | | |
| | | 3 | | | | |
| | | 4 | | | | |
| | | ⋮ | | | | |

| ID | Degree of stereoscopy | Evaluation interval No. | Evaluation interval time | Time duration | Convergence amount distribution | | | |
|---|---|---|---|---|---|---|---|---|
| | | | | | 0 - 10 | 10 - 20 | 20 - 30 | 30 - 40 |
| 1 | 2 | 1 | 00:01:00-00:06:00 | 05:00 | 02:30 | 01:30 | 01:00 | 00:00 |
| | | 2 | 01:00:00-01:05:00 | 05:00 | 02:00 | 02:00 | 01:00 | 00:00 |
| | | 3 | 01:30:00-01:35:00 | 05:00 | 01:00 | 02:30 | 01:30 | 00:00 |
| | | 4 | 02:00:00-02:05:00 | 05:00 | 02:30 | 01:30 | 01:00 | 00:00 |
| ... | ... | ... | ... | ... | | | | |

901 902 903 904 905 906

| ID | Degree of stereoscopy | Evaluation interval No. | Evaluation interval time | Time duration | Convergence amount distribution | | | |
|---|---|---|---|---|---|---|---|---|
| | | | | | 0 - 10 | 10 - 20 | 20 - 30 | 30 - 40 |
| 1 | 3 | | | | | | | |

| ID | Degree of stereoscopy | Evaluation interval No. | Evaluation interval time | Time duration | Convergence amount distribution | | | |
|---|---|---|---|---|---|---|---|---|
| | | | | | 0 - 10 | 10 - 20 | 20 - 30 | 30 - 40 |
| 2 | 1 | | | | | | | |

FIG. 18

| ID | Degree of stereoscopy | Distance from screen | Evaluation interval No. | Evaluation interval time | Time duration | Convergence amount distribution | | | |
|---|---|---|---|---|---|---|---|---|---|
| | | | | | | 0 - 10 | 10 - 20 | 20 - 30 | 30 - 40 |
| 1 | 3 | 150 | 1 | 00:01:00-00:06:00 | 05:00 | 02:30 | 01:30 | 00:00 | 00:00 |
| | | | 2 | 01:00:00-01:05:00 | 05:00 | 02:00 | 02:00 | 01:00 | 00:00 |
| | | | 3 | 01:30:00-01:35:00 | 05:00 | 01:00 | 02:30 | 01:30 | 00:00 |
| | | | 4 | 02:00:00-02:05:00 | 05:00 | 02:30 | 01:30 | 01:00 | 00:00 |
| ... | | | | | | | | | |

| ID | Degree of stereoscopy | Distance from screen | Evaluation interval No. | Evaluation interval time | Time duration | Convergence amount distribution | | | |
|---|---|---|---|---|---|---|---|---|---|
| | | | | | | 0 - 10 | 10 - 20 | 20 - 30 | 30 - 40 |
| 1 | 3 | 50 | | | | | | | |

| ID | Degree of stereoscopy | Distance from screen | Evaluation interval No. | Evaluation interval time | Time duration | Convergence amount distribution | | | |
|---|---|---|---|---|---|---|---|---|---|
| | | | | | | 0 - 10 | 10 - 20 | 20 - 30 | 30 - 40 |
| 1 | 3 | 100 | | | | | | | |

| ID | Degree of stereoscopy | Distance from screen | Evaluation interval No. | Evaluation interval time | Time duration | Convergence amount distribution | | | |
|---|---|---|---|---|---|---|---|---|---|
| | | | | | | 0 - 10 | 10 - 20 | 20 - 30 | 30 - 40 |
| 1 | 3 | 200 | | | | | | | |

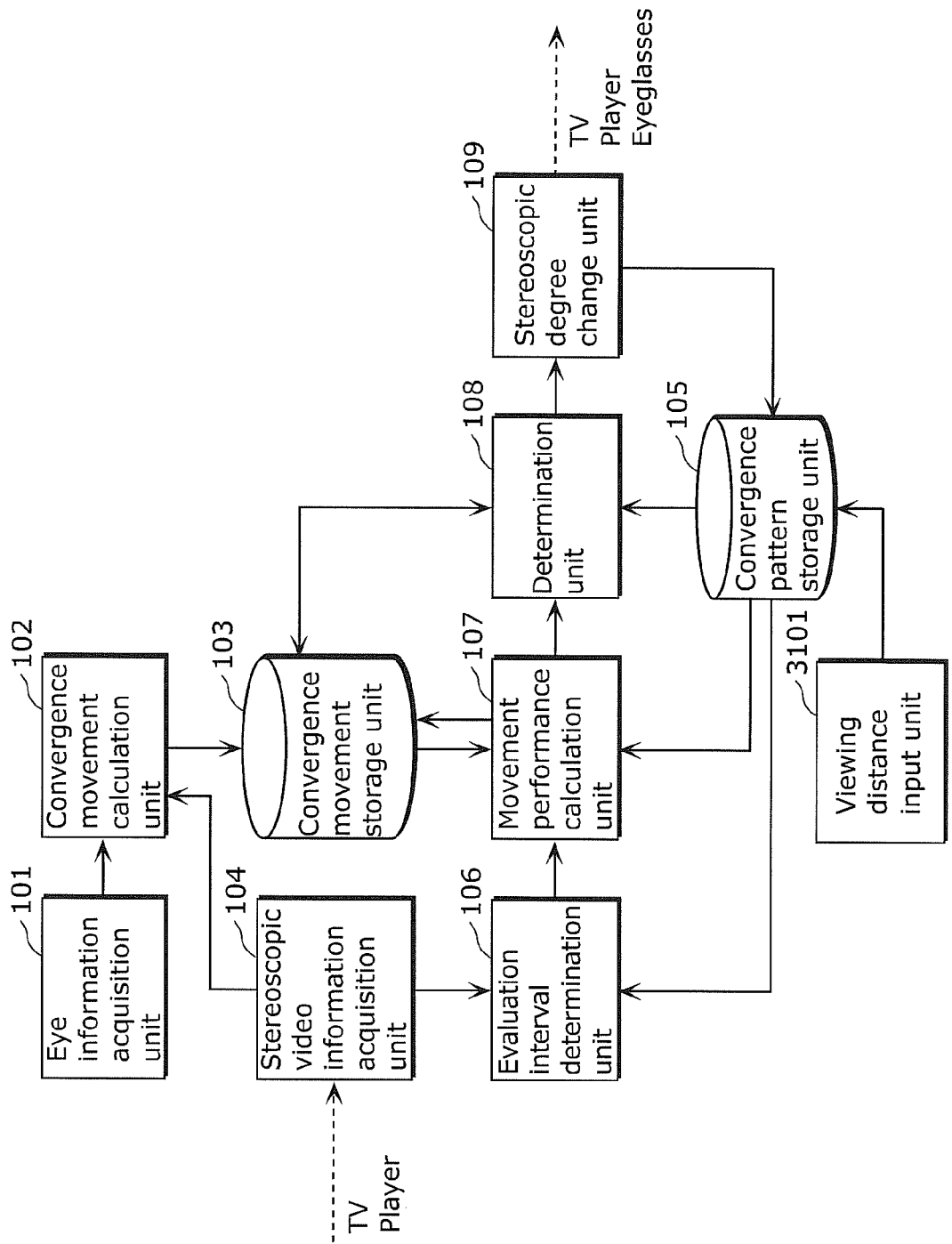

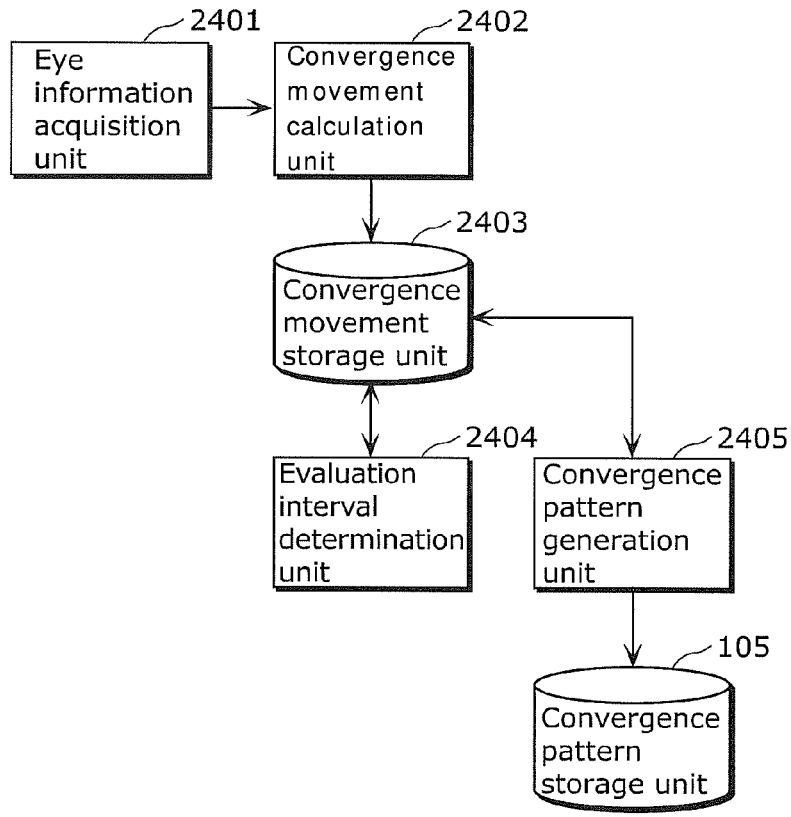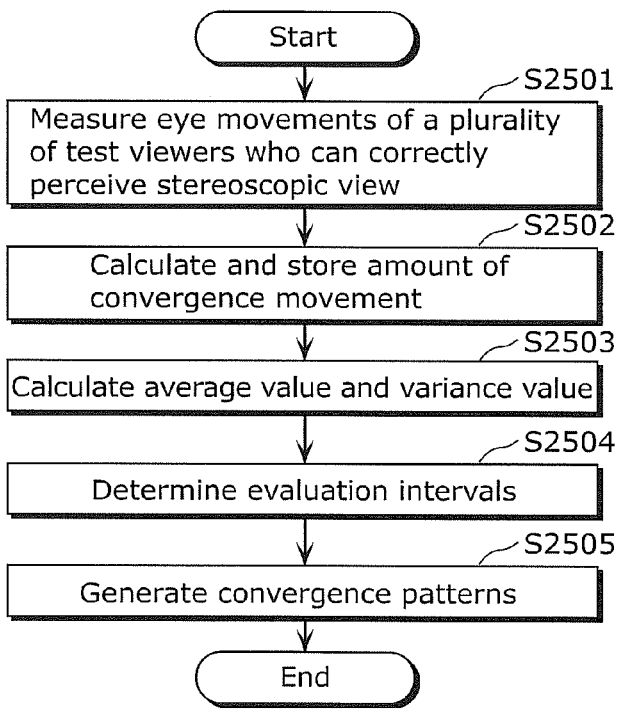

FIG. 24

| Video ID | Degree of stereoscopy | Elapsed time | Amount of convergence (ID1) | Amount of convergence (ID2) | ... | Average value | Variance value |
|---|---|---|---|---|---|---|---|
| 1 | 3 | 00:00:01 | 1.87 | 1.87 | ... | 1.87 | 0.01 |
| | | 00:00:02 | 2.17 | 2.20 | ... | 2.18 | 0.04 |
| | | 00:00:03 | 2.19 | 2.18 | ... | 2.18 | 0.01 |
| | | 00:00:04 | 2.00 | 2.01 | ... | 2.00 | 0.01 |
| | | 00:00:05 | 2.33 | 2.35 | ... | 2.34 | 0.04 |
| | | 00:00:06 | 2.65 | 2.68 | ... | 2.66 | 0.06 |
| | | 00:00:07 | 2.70 | 1.40 | ... | 2.20 | 0.64 |
| | | 00:00:08 | 2.71 | 1.43 | ... | 2.20 | 0.40 |
| | | 00:00:09 | 2.31 | 1.29 | ... | 1.86 | 0.25 |
| | | 00:00:10 | 2.86 | 0.98 | ... | 1.77 | 0.49 |
| | | 00:00:11 | 2.54 | 1.22 | ... | 1.95 | 0.36 |
| | | ... | ... | ... | ... | ... | ... |

2701 — Video ID
2702 — Degree of stereoscopy
2703 — Elapsed time
2704 — Amount of convergence
2705 — Average value
2706 — Variance value

FIG. 25

| Video ID | Test viewer ID | Evaluation interval No. | Evaluation interval time | Time duration |
|---|---|---|---|---|
| 1 | 3 | 1 | 00:01:00-00:06:00 | 05:00 |
| | | 2 | 01:00:00-01:05:00 | 05:00 |
| | | 3 | 01:30:00-01:35:00 | 05:00 |
| | | 4 | 02:00:00-02:05:00 | 05:00 |
| | | ⋮ | ⋮ | ⋮ |

2801, 2802, 2803, 2804, 2805

FIG. 26
(a) Amount of convergence (pixel)
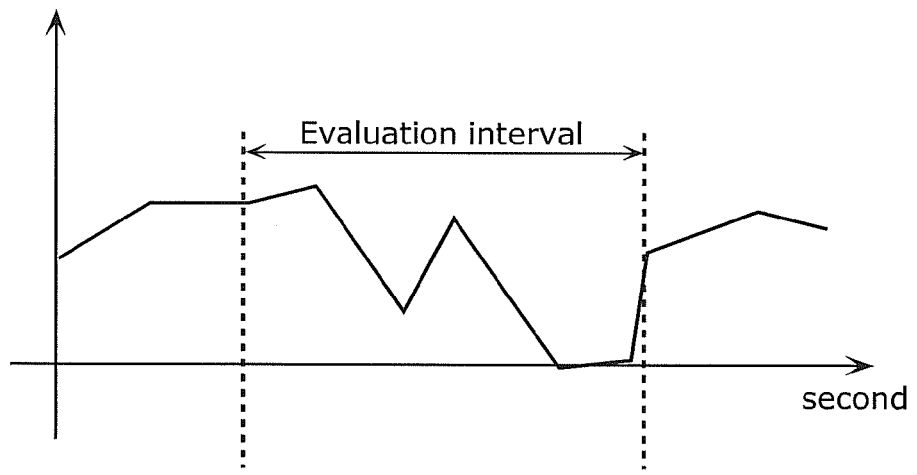
(b) Rate of convergence (pixel/second)
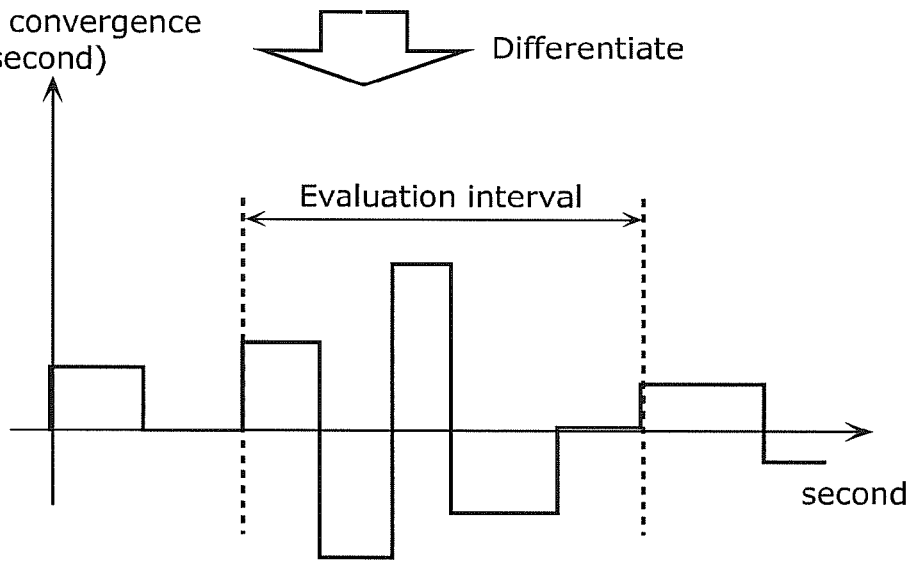
Differentiate

FIG. 27

| ID | Degree of stereoscopy | Evaluation interval No. | Evaluation interval time | Time duration | Convergence rate distribution | | | |
|---|---|---|---|---|---|---|---|---|
| | | | | | 0 - 5 | 5 - 10 | 10 - 15 | 15 - 20 |
| 1 | 3 | 1 | 00:01:00-00:06:00 | 05:00 | 02:30 | 01:00 | 01:00 | 00:30 |
| | | 2 | 01:00:00-01:05:00 | 05:00 | 02:00 | 01:30 | 01:00 | 00:30 |
| | | 3 | 01:30:00-01:35:00 | 05:00 | 01:00 | 01:30 | 01:30 | 01:00 |
| | | 4 | 02:00:00-02:05:00 | 05:00 | 02:30 | 01:00 | 01:00 | 00:30 |
| | | ... | | ... | | | | |

| ID | Degree of stereoscopy | Evaluation interval No. | Measured convergence rate distribution | | | |
|----|----|----|----|----|----|----|
| | | | 0-5 | 5-10 | 10-15 | 15-20 |
| 1 | 3 | 1 | 02:30 | 01:00 | 01:00 | 00:30 |
| | | 2 | | | | |
| | | 3 | | | | |
| | | 4 | | | | |
| | | ⋮ | | | | |

2301, 2302, 2303, 2304

FIG. 30
| ID | Evaluation interval No. | Evaluation interval time | Time duration |
|---|---|---|---|
| 1 | 1 | 00:01:00-00:06:00 | 05:00 |
|   | 2 | 01:00:00-01:05:00 | 05:00 |
|   | 3 | 01:30:00-01:35:00 | 05:00 |
|   | 4 | 02:00:00-02:05:00 | 05:00 |
|   | ⋮ | ⋮ | ⋮ |
FIG. 31
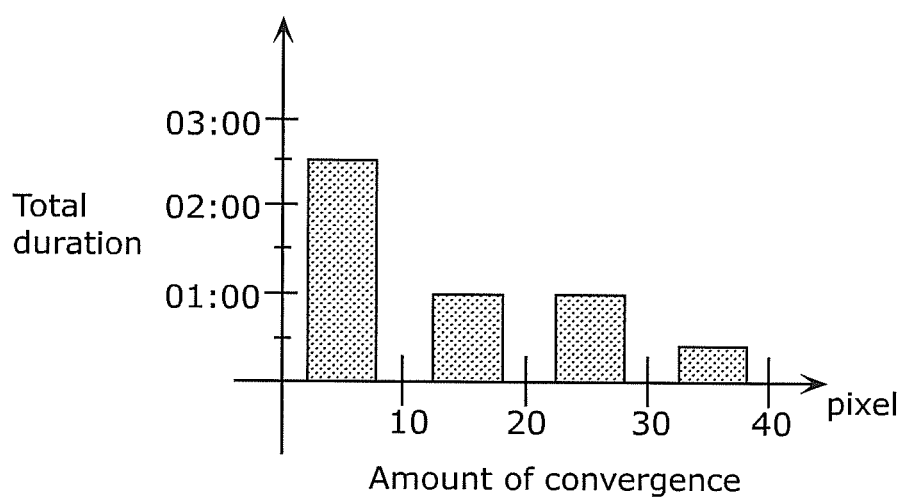
FIG. 32
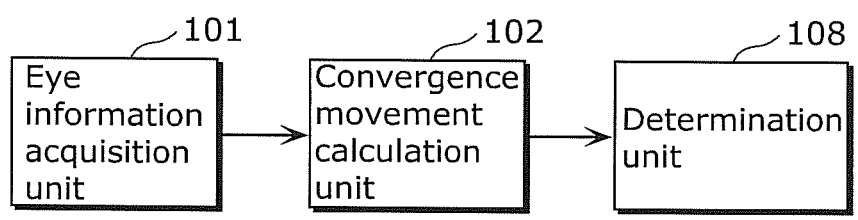

DEVICE AND METHOD FOR DETERMINING CONVERGENCE EYE MOVEMENT PERFORMANCE OF A USER WHEN VIEWING A STEREOSCOPIC VIDEO

CROSS REFERENCE TO RELATED APPLICATIONS

This is a continuation application of PCT Patent Application No. PCT/JP 2012/002345 filed on Apr. 4, 2012, designating the United States of America, which is based on and claims priority of Japanese Patent Application No. 2011-112680 filed on May. 19, 2011. The entire disclosures of the above-identified applications, including the specifications, drawings and claims are incorporated herein by reference in their entirety.

FIELD

One or more exemplary embodiments disclosed herein relate generally to a convergence performance determination device which allows determination of convergence eye movement performance of a user viewing a stereoscopic video.

BACKGROUND ART

A method utilizing the binocular parallax is known as a method for allowing a user to view a video displayed on a flat-panel display as a stereoscopic video. This is a method which utilizes a fact that a user perceives the depth because the user's right and left eyes are positioned away from each other and videos in the left eye and right eye have different viewpoints.

The method utilizing the binocular parallax allows a user to perceive stereoscopy in the user's brain by displaying different videos to the user's right and left eyes. However, such a stereoscopic view achieved by a method apart from reality may give the user visual fatigue or a sense of discomfort.

Thus, a stereoscopic video display apparatus is proposed which estimates the level of fatigue, based on a reduced amount in visual function due to fatigue of the eyes, and adjusts, in accordance with the estimated level of fatigue, the degree of stereoscopy (a value indicative of the degree of stereoscopy) (for example, see PTL 1).

CITATION LIST

Patent Literature

[PTL 1] Japanese Unexamined Patent Application Publication No. H9-18894

SUMMARY

Technical Problem

In PTL 1, user fatigue is detected based on the number of times the eye convergence is performed or the number of abnormal phenomena in which the vergence of the left and right eyes breaks down during a period of time, and the degree of stereoscopy is changed. In addition, the degree of stereoscopy is changed by decreasing the degree of stereoscopy by one step when the user fatigue is detected.

Meanwhile, whether the user is able to perceive the stereoscopic view depends on the convergence eye movement performance of the user. Specifically, the greater the degree of stereoscopy, the larger the convergence movement required for the user to view the video. Thus, in the stereoscopic video which includes various degrees of stereoscopy, a user having a low convergence movement performance is unable to correctly perceive the stereoscopic video that has a degree of stereoscopy greater than a certain degree of stereoscopy. If the user continuously views the stereoscopic video that requires the user for much more than the convergence eye movement performance of the user, the user may feel fatigued or a sense of discomfort.

However, measuring the number of times the eye convergence is performed or the number of abnormal phenomena, in which the vergence of the left and right eyes breaks down, during a period of time with respect to the user viewing the video having a degree of stereoscopy with which the user is unable to correctly perceive the stereoscopic view as described in PTL 1 is undesirably considered as measuring the level of fatigue due to the video having the degree of stereoscopy with which the user is able to correctly perceive the video, instead of considering as measuring the fatigue due to the video having the degree of stereoscopy with which the user is unable to correctly perceive the stereoscopic view. Thus, it is difficult to correctly detect the fatigue and the sense of discomfort caused by the video having the degree of stereoscopy with which the user is unable to correctly perceive the stereoscopic view. Additionally, it is difficult to change the degree of stereoscopy prior to the occurrence of the fatigue.

Moreover, in PTL 1, the degree of stereoscopy is decreased by one step each time fatigue is detected, which requires a predetermined time for detection of fatigue. Therefore, if the degree of stereoscopy of the stereoscopic video is significantly greater than the convergence eye movement performance of the user, it takes considerable amount of time to decrease the degree of stereoscopy down to a degree of stereoscopy suitable for the user, which ends up providing increased fatigue to the user.

One non-limiting and exemplary embodiment provides a convergence performance determination device which allows a degree of stereoscopy of a stereoscopic video to be changed to a degree of stereoscopy suitable for a user.

Solution to Problem

In one general aspect, the techniques disclosed here feature a convergence performance determination device including an eye information acquisition unit configured to acquire eye information which is information on eye movements of a user when viewing a stereoscopic video; a convergence movement calculation unit configured to calculate amounts of convergence movement each indicating a degree of a convergence eye movement of the user, based on the eye information acquired by the eye information acquisition unit; and a determination unit configured to determine convergence eye movement performance of the user by comparing between distribution data indicating a distribution of the amounts of convergence movement calculated by the convergence movement calculation unit in an evaluation interval which is a predetermined playback time interval of the stereoscopic video being viewed by the user and distribution data indicating a distribution of the amounts of convergence movement determined in accordance with depth information on the stereoscopic video in the evaluation interval.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

A convergence performance determination device according to one or more exemplary embodiments or features disclosed herein can be provided which determines, in each degree of stereoscopy, convergence movement performance of a user viewing a stereoscopic video, and, based on the result, allows the degree of stereoscopy of the stereoscopic video to be changed to a degree of stereoscopy suitable for the user.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 1 is a diagram illustrating eyeglasses control principles which enables stereoscopic view.

FIG. 7 is a diagram showing an example of data of convergence movements stored in a convergence movement storage unit.

FIG. 12 is a diagram showing an example of a convergence amount distribution stored in the convergence pattern storage unit.

FIG. 13 is a diagram showing an example of playing video information.

FIG. 14 is a diagram showing an example of a calculation result of convergence movement.

FIG. 17 is a diagram showing an example of convergence patterns stored in the convergence pattern storage unit.

FIG. 18 is a diagram showing an example of the convergence patterns for different viewing distances.

FIG. 20 is a block diagram showing a functional configuration of another convergence performance determination device according to the exemplary embodiment.

FIG. 21 is a block diagram showing a functional configuration of a convergence pattern generation device according to the exemplary embodiment.

FIG. 22 is a flowchart illustrating operation of the convergence pattern generation device.

FIG. 24 is a diagram showing data of average values and variance values of the amounts of convergence stored in the convergence movement storage unit.

FIG. 25 is a diagram showing an example of information on the evaluation intervals stored in the convergence movement storage unit.

FIG. 26 is a diagram illustrating a method of calculating a convergence rate distribution.

FIG. 27 is a diagram showing an example of the convergence patterns.

FIG. 28 is a diagram showing an example of a measured convergence rate distribution stored in the convergence movement storage unit.

FIG. 30 is a diagram showing an example of the convergence patterns stored in the convergence pattern storage unit.

FIG. 31 is a diagram showing an example of an ideal convergence amount distribution.

FIG. 32 is a block diagram showing a functional configuration of the convergence performance determination device which includes essential components of the present disclosure.

DESCRIPTION OF EMBODIMENT

Figure 2A:
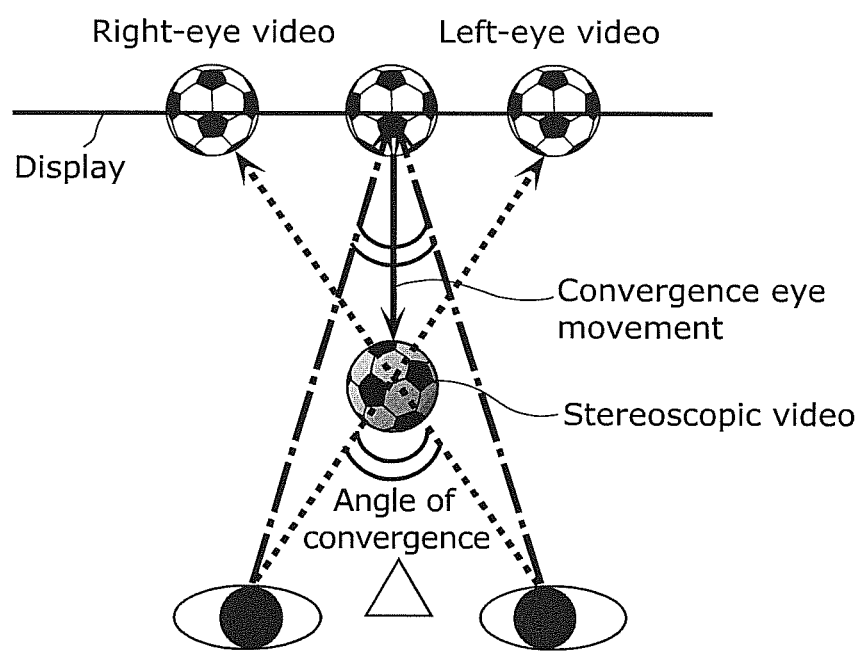
FIG. 2A is a diagram illustrating an angle of convergence in stereoscopic view.

Hereinafter, exemplary embodiments will be described with reference to the accompanying drawings.

A convergence performance determination device according to an exemplary embodiment disclosed herein includes an eye information acquisition unit configured to acquire eye information which is information on eye movements of a user when viewing a stereoscopic video; a convergence movement calculation unit configured to calculate amounts of convergence movement each indicating a degree of a convergence eye movement of the user, based on the eye information acquired by the eye information acquisition unit; and a determination unit configured to determine convergence eye movement performance of the user by comparing between distribution data indicating a distribution of the amounts of convergence movement calculated by the convergence movement calculation unit in an evaluation interval which is a predetermined playback time interval of the stereoscopic video being viewed by the user and distribution data indicating a distribution of the amounts of convergence movement determined in accordance with depth information on the stereoscopic video in the evaluation interval.

According to the above configuration, the amount of the convergence eye movement of the user viewing the stereoscopic view are calculated from the eye information on the user viewing the stereoscopic video and the distribution of the amounts of convergence movement is compared with an ideal distribution of the amounts of convergence movement in the evaluation interval, thereby determining the convergence eye movement performance of the user. Thus, the convergence movement performance of the user viewing the stereoscopic video can be determined in each degree of stereoscopy and, based on the result, the degree of stereoscopy of the stereoscopic video can be changed to a degree of stereoscopy suitable for the user. As such, by changing the degree of stereoscopy based on the determination result, the stereoscopic video having the degree of stereoscopy suitable for the user can be presented to the user by changing the degree of stereoscopy by one step. Thus, a stereoscopic video making the user feel low fatigue and low sense of discomfort can be presented to the user.

It should be noted that a convergence performance determination device disclosed in the exemplary embodiment is applicable not only to stereoscopic videos but also to stereoscopic images such as still images.

Moreover, for each of segments obtained by dividing a range of possible values of the amounts of convergence movement in the evaluation interval, the determination unit may compare an integration time of the amounts of convergence movement calculated by the convergence movement calculation unit that fall within the segment and an integration time of the amounts of convergence movement determined in accordance with the depth information on the stereoscopic video that fall within the segment, to determine the convergence eye movement performance of the user.

According to the above configuration, the range of the amounts of convergence movement having low convergence movement performance can accurately be specified.

Moreover, the determination unit may determine that the convergence eye movement performance of the user is low in a segment in which the integration time of the amounts of convergence movement calculated by the convergence movement calculation unit is smaller than the integration time of the amounts of convergence movement determined in accordance with the depth information on the stereoscopic video, the segment being included in the segments.

Moreover, for each of segments obtained by dividing a range of possible values of the amounts of convergence movement in the evaluation interval, the determination unit may compare information indicating whether the amounts of convergence movement calculated by the convergence movement calculation unit fall within the segment and information indicating whether the amounts of convergence movement determined in accordance with the depth information on the stereoscopic video fall within the segment, to determine the convergence eye movement performance of the user.

According to the above configuration, for each of the segments obtained by dividing a range of possible values of the amounts of convergence movement in the evaluation interval, the convergence performance determination device may store only information as to whether the amount of convergence movement falls within the segment. Thus, the information stored in the convergence performance determination device can be reduced in size. Moreover, the determination unit determines whether the amount of convergence movement falls within the segment, instead of comparing the lengths of the amounts of convergence movement. Thus, the complexity of the determination unit can be reduced.

Moreover, the evaluation interval may be the playback time interval of the stereoscopic video when variance values of the amounts of convergence movement of a plurality of test viewers viewing the stereoscopic video are continuously less than or equal to a predetermined value for a predetermined time or longer.

According to the above configuration, it is assured that there are no multiple subjects whereby the users are caused to have different amounts of convergence movement in the evaluation interval for which the stereoscopic video is displayed. In other words, when there are multiple subjects having different depths in the stereoscopic video, subjects watched by the test viewers may be different. In such a case, the amounts of convergence eye movements are different among the test viewers, and thus the variance value of the amounts of convergence movement is large. In contrast, if the stereoscopic video includes only one subject to be watched, the amounts of convergence eye movements among the test viewers are substantially the same, and thus the variance value of the amounts of convergence movement is small. Therefore, setting the playback time interval in which the variance value of the amounts of convergence movement is small to the evaluation interval allows accurate determination of the convergence movement performance of the users.

A convergence performance determination device according to another exemplary embodiment disclosed herein is a convergence performance determination device for determining convergence eye movement performance of a user, based on a state of the eyes of the user when viewing a stereoscopic video, the convergence performance determination device including: an eye information acquisition unit configured to acquire eye information which is information on eye movements of the user when viewing the stereoscopic video; a convergence movement calculation unit configured to calculate amounts of convergence movement each indicating a degree of a convergence eye movement of the user, based on the eye information acquired by the eye information acquisition unit; and a determination unit configured to compare distribution data indicating a distribution of the amounts of convergence movement calculated by the convergence movement calculation unit in a first evaluation interval which is a predetermined playback time interval of the stereoscopic video being viewed by the user and distribution data indicating a distribution of the amounts of convergence movement calculated by the convergence movement calculation unit in a second evaluation interval which is different from the first evaluation interval and a predetermined playback time interval of the stereoscopic video being viewed by the user, to determine the convergence eye movement performance of the user.

For example, distribution data indicating the distribution of the amounts of convergence movement determined in accordance with depth information on the stereoscopic video in the first evaluation interval and distribution data indicating the distribution of the amounts of convergence movement determined in accordance with the depth information on the stereoscopic video in the second evaluation interval are the same.

According to the above configuration, the amount of the convergence eye movement of the user viewing the stereoscopic view is calculated from the eye information on the user viewing the stereoscopic video and the distribution of the amounts of convergence movement is compared with distribution of the amounts of convergence movement in other evaluation interval, thereby determining the convergence eye movement performance of the user. Thus, the deterioration in convergence movement performance of the user viewing the stereoscopic video can be determined in each degree of stereoscopy and, based on the result, the degree of stereoscopy of the stereoscopic video can be changed to a degree of stereoscopy suitable for the user. As such, by changing the degree of stereoscopy based on the determination result, the stereoscopic video having the degree of stereoscopy suitable for the user can be presented to the user by changing the degree of stereoscopy by one step. Thus, a stereoscopic video making the user feel low fatigue and low sense of discomfort can be presented to the user.

Moreover, the amounts of convergence movement may be amounts of convergence indicating values corresponding to pupillary distances between the left eye and the right eye of the user.

Moreover, the amounts of convergence movement may be convergence rates indicating time variations in amount of convergence indicating values corresponding to pupillary distances between the left eye and the right eye of the user.

Moreover, the convergence performance determination device may further include a stereoscopic degree change unit configured to change a degree of stereoscopy of the stereoscopic video so as not to cause the convergence movement the amounts of convergence in which is determined to have a low convergence movement performance by the determination unit.

These general and specific aspects may be implemented using a system, a method, an integrated circuit, a computer program, or a computer-readable recording medium such as a CD-ROM, or any combination of systems, methods, integrated circuits, computer programs, or computer-readable recording media Next, eyeglasses control principles which enables a stereoscopic view will be described.

Examples of an apparatus which presents a stereoscopic video to a user include an apparatus, as shown in FIG. 1, in which a right-eye video and a left-eye video are alternately displayed on a display (hereinafter, such videos will be described as "stereoscopic video"), and liquid crystal shutter glasses for stereoscopic viewing alternately pass the right-eye video and the left-eye video through a right shutter and a left shutter, respectively, in synchronization with the display of the stereoscopic video, thereby presenting, to a user, videos corresponding to the left and right eyes of the user (the frame sequential method). In other words, a shutter synchronization control of the shutter glasses is performed so that the left-eye video is displayed to the left eye and the right-eye video is displayed to the right eye. By displaying different videos to the left and right eyes using such a device, the user is allowed to perceive the stereoscopic view.

Figure 2B:
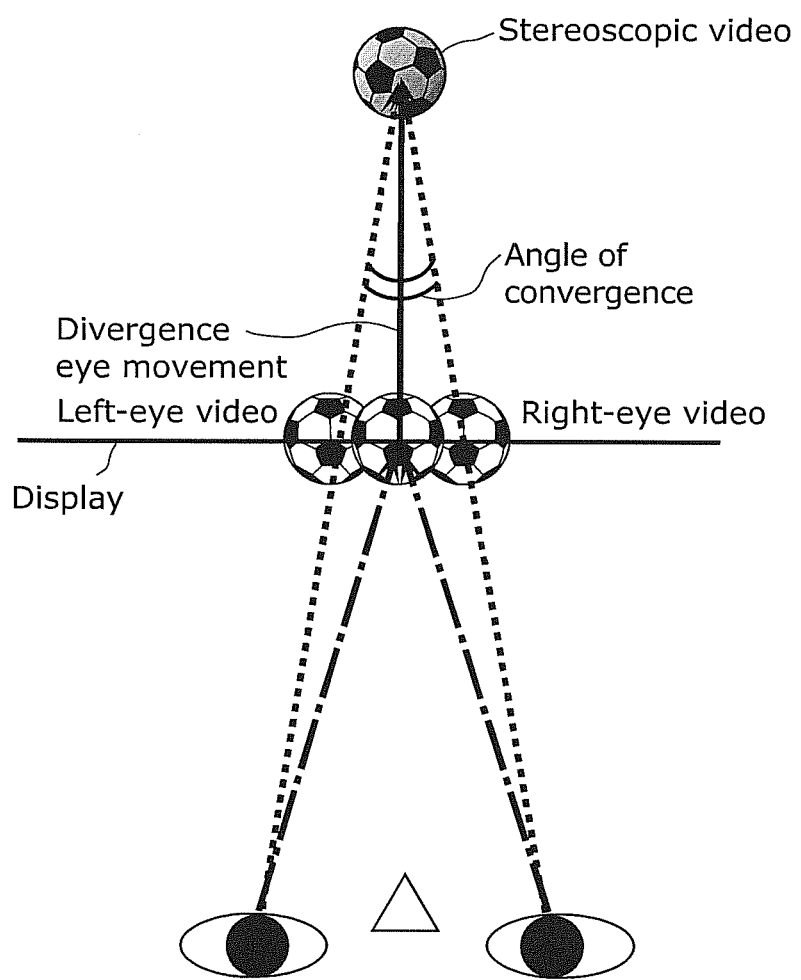
FIG. 2B is a diagram illustrating an angle of convergence in the stereoscopic view.

Here, the eye movement of a user viewing the stereoscopic video will briefly be described. When different videos are displayed to the left and right eyes using the stereoscopic video as described above, the user is allowed to perceive the degree of stereoscopy in terms of depth by being allowed to view different videos in the horizontal direction. Here, as shown in FIG. 2A, the greater a distance (disparity) between an object rightward away from the left eye in the left-eye video and the object leftward away from the right eye in the right-eye video, the closer the displayed object appears to the user (hereinafter, expressed as "an increased degree of stereoscopy"), and the eyes of the user at the time rotate toward each other. This movement is called convergence eye movement, and an angle between viewing directions of the eyes is called an angle of convergence. The angle of convergence is an amount indicating how inwardly the pupils of the left and right eyes are positioned toward each other (relative to a state in which the left and right eyes are looking at the distance at infinity), and, as can be seen from FIG. 2A, the closer the three-dimensionally perceived location of an object is to the eyes, the greater the angle of convergence is. On the other hand, as the three-dimensionally perceived location of an object stereoscopically displayed as shown in FIG. 2B is away from the eyes, the pupils of the eyes of the user rotate away from each other. This movement is called divergence eye movement. The angle of convergence is small at the divergence eye movement.

The convergence performance determination device according to the present embodiment calculates amounts of the convergence movement, which indicate degrees of convergence movement for different convergence angles of a user viewing the stereoscopic video, to determine the convergence eye movement performance of the user. In the present embodiment, however, as the amount of convergence movement, the amount of convergence correlated to the angle of convergence is calculated and used, instead of calculating the angle of convergence of the eyes.

Hereinafter, an example of the embodiment according to the exemplary embodiment which determines convergence eye movement performance of the user, based on a result obtained by measuring the convergence movements for different convergence amounts of the user, to control the liquid crystal shutter glasses will be described with reference to the accompanying drawings. It should be noted that while the convergence movement will be described as the eye movement of the user in the present embodiment, the divergence eye movement can also be measured by the same method.

Hereinafter, certain exemplary embodiments are described in greater detail with reference to the accompanying Drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

Figure 3:
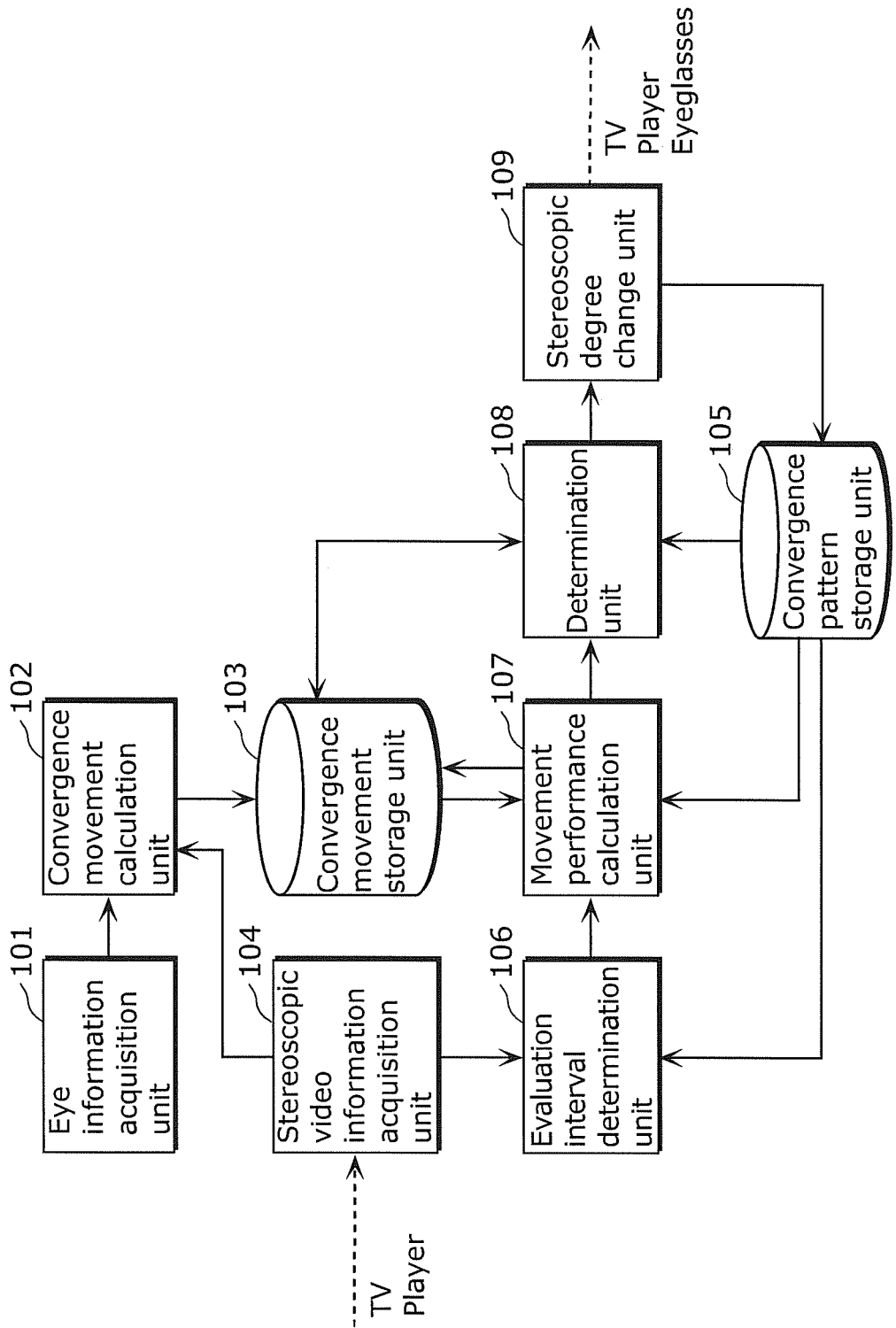
FIG. 3 is a block diagram showing a functional configuration of a convergence performance determination device according to an exemplary embodiment.

FIG. 3 is a block diagram showing a functional configuration of the convergence performance determination device according to the exemplary embodiment.

The convergence performance determination device includes an eye information acquisition unit 101, a convergence movement calculation unit 102, a convergence movement storage unit 103, a stereoscopic video information acquisition unit 104, a convergence pattern storage unit 105, an evaluation interval determination unit 106, a movement performance calculation unit 107, a determination unit 108, and a stereoscopic degree change unit 109.

The eye information acquisition unit 101 uses a sensor such as a camera or electrodes to acquire eye information of a user viewing a stereoscopic video. The eye information is information on the eye movement.

The convergence movement calculation unit 102 calculates the amount of convergence movement of the eye movement, based on the eye information acquired by the eye information acquisition unit 101 and stores the obtained amount of convergence movement of the eye movement in the convergence movement storage unit 103.

The stereoscopic video information acquisition unit 104 acquires information on a currently displayed stereoscopic video from, for example, a TV displaying the stereoscopic video or a player playing back the stereoscopic video. The stereoscopic video information acquisition unit 104 acquires, for example, the title of the stereoscopic video, degrees of stereoscopy representing the degrees of stereoscopy throughout the playback of the currently displayed stereoscopic video, or elapsed time since a start time of the stereoscopic video.

The convergence pattern storage unit 105 stores therein information on ideal convergence in the currently displayed stereoscopic video.

The evaluation interval determination unit 106 determines a time interval the convergence movement in which is to be evaluated. Hereinafter, the time interval is sometimes referred to simply as interval.

The movement performance calculation unit 107 calculates stereoscopic viewing times for different amounts of convergence in the interval determined by the evaluation interval determination unit 106, based on the amount of convergence movement calculated by the convergence movement calculation unit 102.

The determination unit 108 determines the convergence eye movement performance of the user, based on a result obtained by comparing a result calculated by the movement performance calculation unit 107 with the information on ideal convergence stored in the convergence pattern storage unit 105.

The stereoscopic degree change unit 109 determines how to change the degree of stereoscopy of the currently displayed stereoscopic video, based on the result determined by the determination unit 108, and stores the result in the convergence pattern storage unit 105 and transmits the result to a device which can change the degree of stereoscopy. Here, examples of the device that can change the degree of stereoscopy include a player playing the stereoscopic video, a TV displaying the stereoscopic video, and eyeglasses (hereinafter, described as "eyeglasses for stereoscopic viewing") required to view the stereoscopic video.

Figure 4:
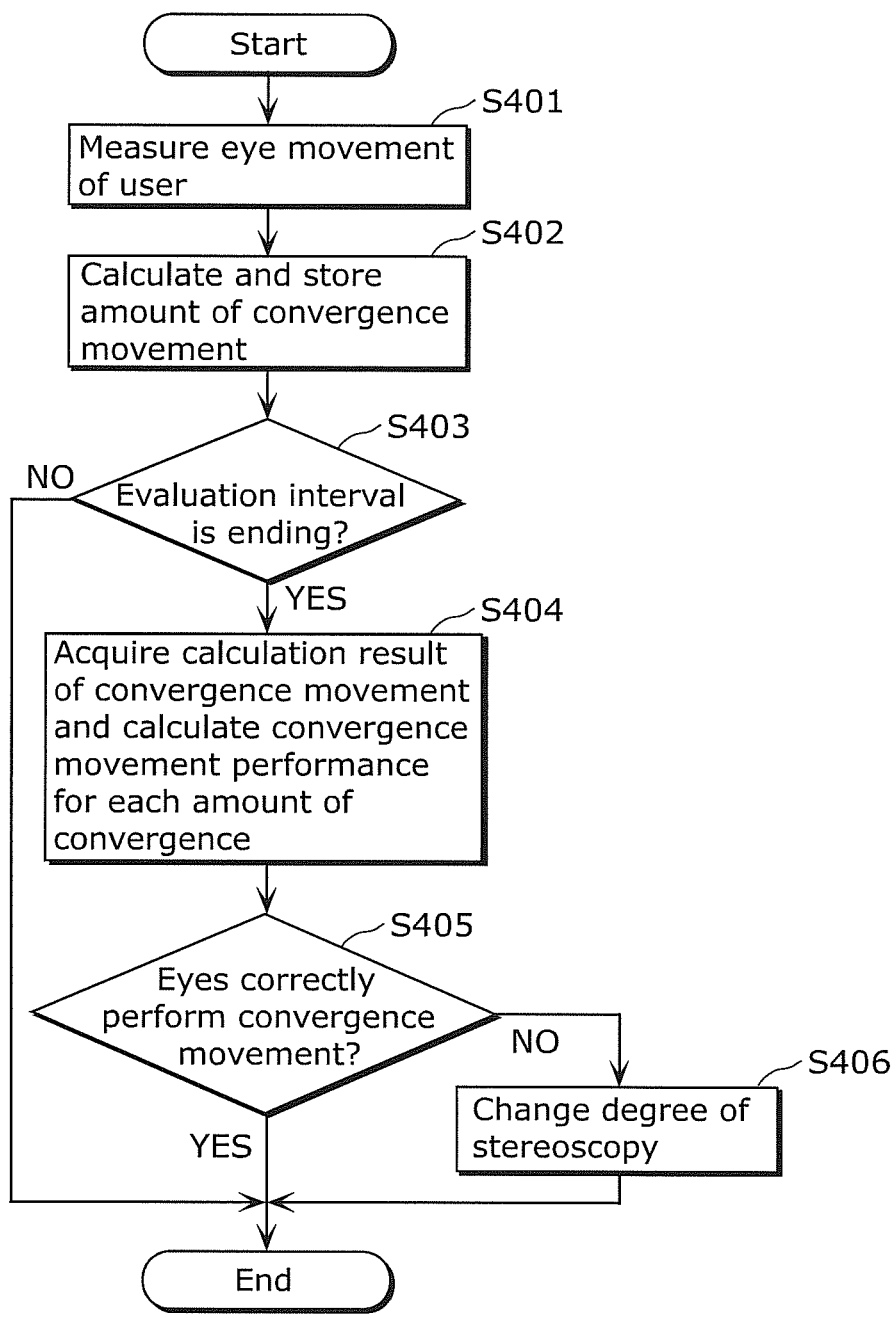
FIG. 4 is a flowchart illustrating operation of the convergence performance determination device according to the exemplary embodiment.

The following will describe the processing performed by the convergence performance determination device, with reference to a flowchart illustrated in FIG. 4.

The processing of the convergence performance determination device illustrated in FIG. 4 is performed from the start of the stereoscopic video to the end at predetermined intervals.

Figure 5A:
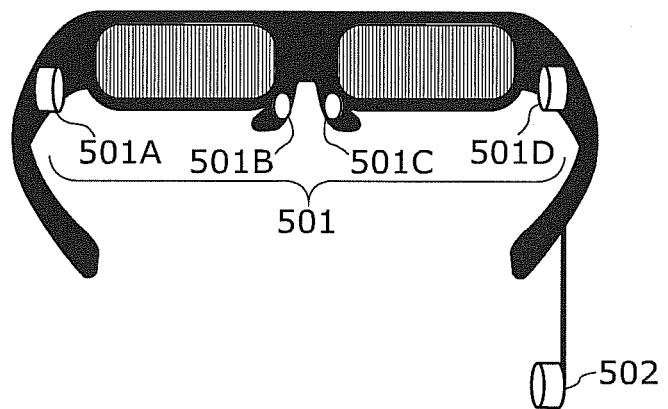
FIG. 5A is a diagram showing an example of eyeglasses for stereoscopic viewing which are used for measuring electrooculograms.
Figure 5B:
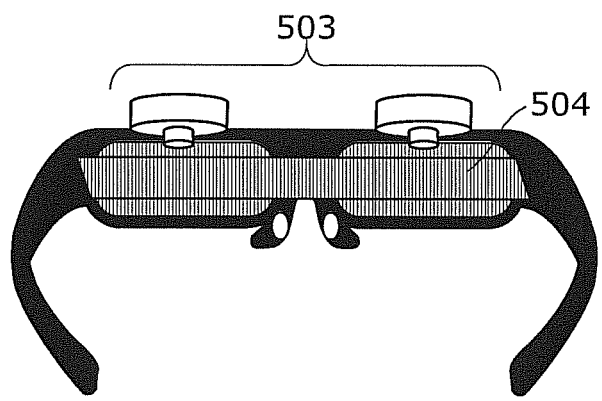
FIG. 5B is a diagram showing an example of eyeglasses for stereoscopic viewing which are used for capturing a video of the eyes.
Figure 5C:
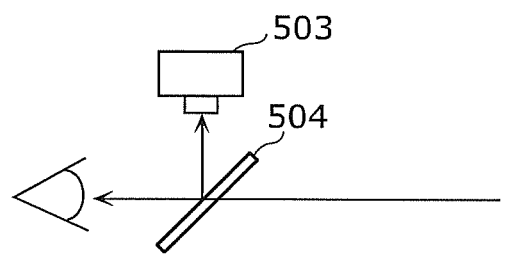
FIG. 5C shows a side view of FIG. 5B without the eyeglasses.

In step S401, the eye information acquisition unit 101 acquires the eye information of the user at predetermined intervals, using the sensor. Here, examples of the method of acquiring the eye information include a method to measure electrooculograms using electrodes as the sensor and measure the potential variations, and a method to capture an eye image using a camera as the sensor. FIG. 5A to FIG. 5C each show an example overview of eyeglasses for stereoscopic viewing which has the sensor such as the electrodes or the camera attached thereto and enables to measure the eye movement.

FIG. 5A shows the eyeglasses for stereoscopic viewing which are used for measuring the electrooculograms, and electrodes 501 and 502 for measuring the electrooculograms are provided on a frame portion of the eyeglasses. The electrodes 501 are electrodes for measuring the potentials of the eyes, and include four electrodes which are an electrode 501A, an electrode 501B, an electrode 501C, and an electrode 501D. The electrode 502 is a ground electrode. Changes in potential of the eyes are measured by a potential difference between the electrodes 501 and the electrode 502. FIG. 5B shows eyeglasses for stereoscopic viewing which are used for capturing the eye image, and include a camera 503 and a half mirror 504. An image of the eyes of the user reflected in the half mirror 504 is captured by the camera 503 attached to the upper portion of the eyeglasses. It should be noted that FIG. 5C shows a side view of FIG. 5B without the eyeglasses. As shown in FIG. 5C, videos are delivered to the user's eyes through the half mirror while the images of the user's eyes reflected in the half mirror enter the camera 503.

The following processing will be described using a case where the eye information of a user as shown in FIG. 5B is obtained by eyeglasses for viewing the stereoscopic video which can capture the eye image.

Figure 6:
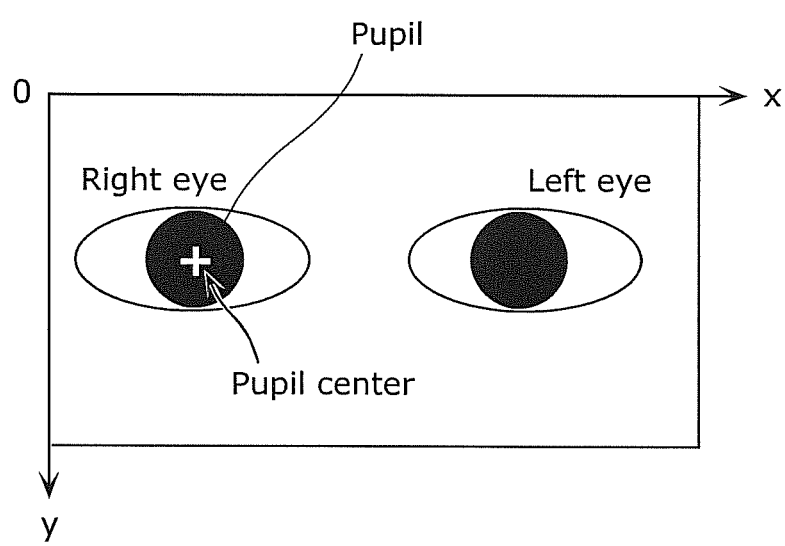
FIG. 6 is a diagram showing an example of an eye image captured as eye information.

The eye information acquisition unit 101 uses the camera 503 to capture images of the user's eyes at predetermined intervals. An example of the captured image is shown in FIG. 6.

In step S402, the convergence movement calculation unit 102 calculates and stores an amount of convergence eye movement of the user in the convergence movement storage unit 103. First, the amount of convergence movement which is calculated by the convergence movement calculation unit 102 will be specifically described. The convergence movement calculation unit 102 extracts an image of pupils by performing image processing on image data of the eyes obtained by the eye information acquisition unit 101, and further calculates pupil center coordinates of the eyes. Among the calculated pupil center coordinates of the eyes, the convergence movement calculation unit 102 calculates an amount of convergence that is calculated from coordinates (x coordinates) in the horizontal direction and values of the x coordinates, and stores the calculated amount of convergence as the amount of convergence movement in the convergence movement storage unit 103. In the present embodiment, a value obtained by subtracting the value of the x coordinate of the right eye from the value of the x coordinate of the left eye is used as the amount of convergence. With such definition of the amount of convergence, the amount of convergence remains always a constant value when a user is looking at an object on the screen while the amount of convergence is smaller than the constant value when the user is looking at an object projected from the screen.

Figure 8:
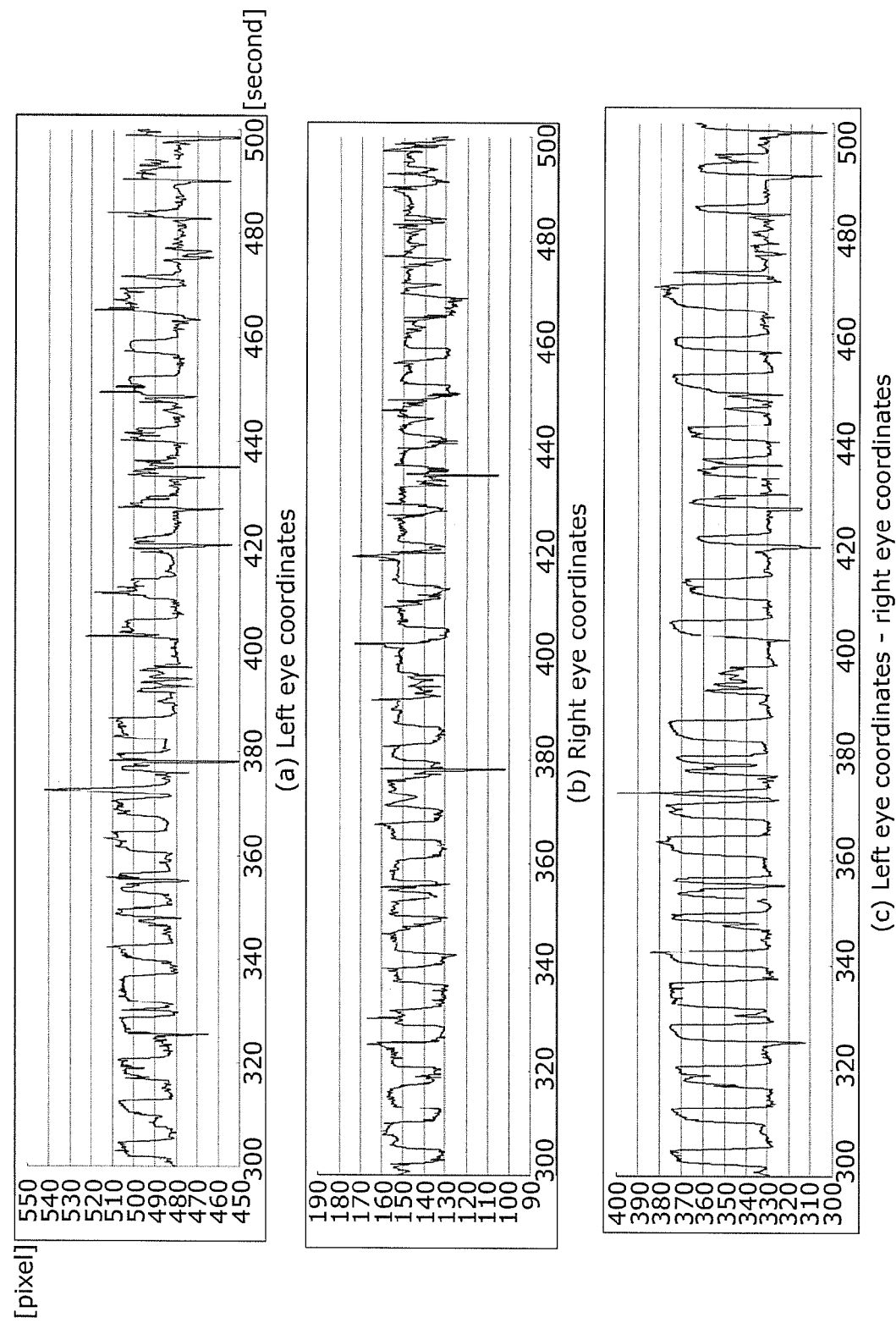
FIG. 8 is a graph showing changes in pupil center positions of the user's eyes over time and a change in amount of convergence over time.
Figure 9:
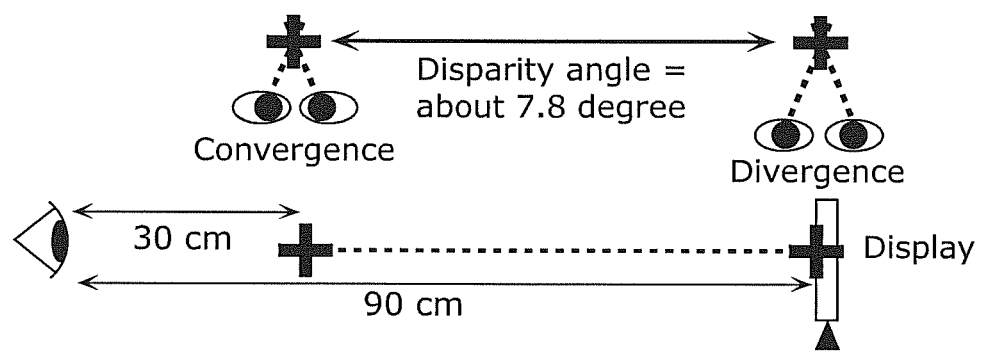
FIG. 9 is a diagram illustrating an experiment performed on a user.

Next, an example of the result of calculating the amount of convergence movement to be stored in the convergence movement storage unit 103 is shown in FIG. 7. The item 701 indicates date and time of the measurement. The item 702 indicates an x coordinate (in pixel units) of the pupil center coordinates of the right eye. The item 703 indicates an x coordinate (in pixel units) of the pupil center coordinates of the left eye. The item 704 indicates the amount of convergence. The amount of convergence is a value (in pixel units) obtained by subtracting a value of the item 702 from a value of the item 703. FIG. 8 shows a result obtained by graphing changes in pupil center positions of the user's eyes over time and changes in the amount of convergence over time when an experiment is performed in which a mark displayed on a screen (display) and a mark displayed at a position, away from the screen, whereby a certain degree of stereoscopy is achieved, as shown in FIG. 9 are alternately shown to the user. Specifically describing the experiment, a cross mark is presented alternately on the screen, which is 90 cm ahead of the user, and at a position 60 cm forward from the screen at 3 second to 5 second intervals for 900 seconds, and the change in the pupil center positions of the eyes over time and the change in the amount of convergence over time then is obtained. Parts (a) and (b) of FIG. 8 show changes in pupil center coordinates of the left eye and the right eye, respectively, over time, and (c) of FIG. 8 indicates the change in the amount of convergence over time obtained by subtracting the pupil center coordinates of the right eye ((b) of FIG. 8) from the pupil center coordinates of the left eye ((a) of FIG. 8) at the same time. In the amount of convergence shown in (c) of FIG. 8, a value being positioned at about a pixel 375 indicates that the user is looking at the mark displayed on the screen, and a value of the amount of convergence being positioned at about a pixel 330 indicates that the user is looking at the mark displayed at the position away from the screen whereby the certain degree of stereoscopy is achieved.

Here, the amount of convergence is defined as reduction of the horizontal pupillary distance between the eyes based on the horizontal pupillary distance between the eyes looking at a non-stereoscopic video on the screen so that the greater the degree of stereoscopy of the video being viewed by the user, the larger the amount of convergence of the user is expressed. For example, it is assumed that in the case where the horizontal pupillary distance between the eyes looking on the screen as shown in FIG. 8 is 375 pixels and the horizontal pupillary distance between the eyes viewing a video at certain time is 365 pixels, the amount of convergence is 10 pixels.

Data stored in the convergence pattern storage unit 105 will be described. In the convergence pattern storage unit 105, data of the ideal convergence amount distribution in one or more evaluation intervals between the start time and end time of the stereoscopic video is stored.

Figure 10:
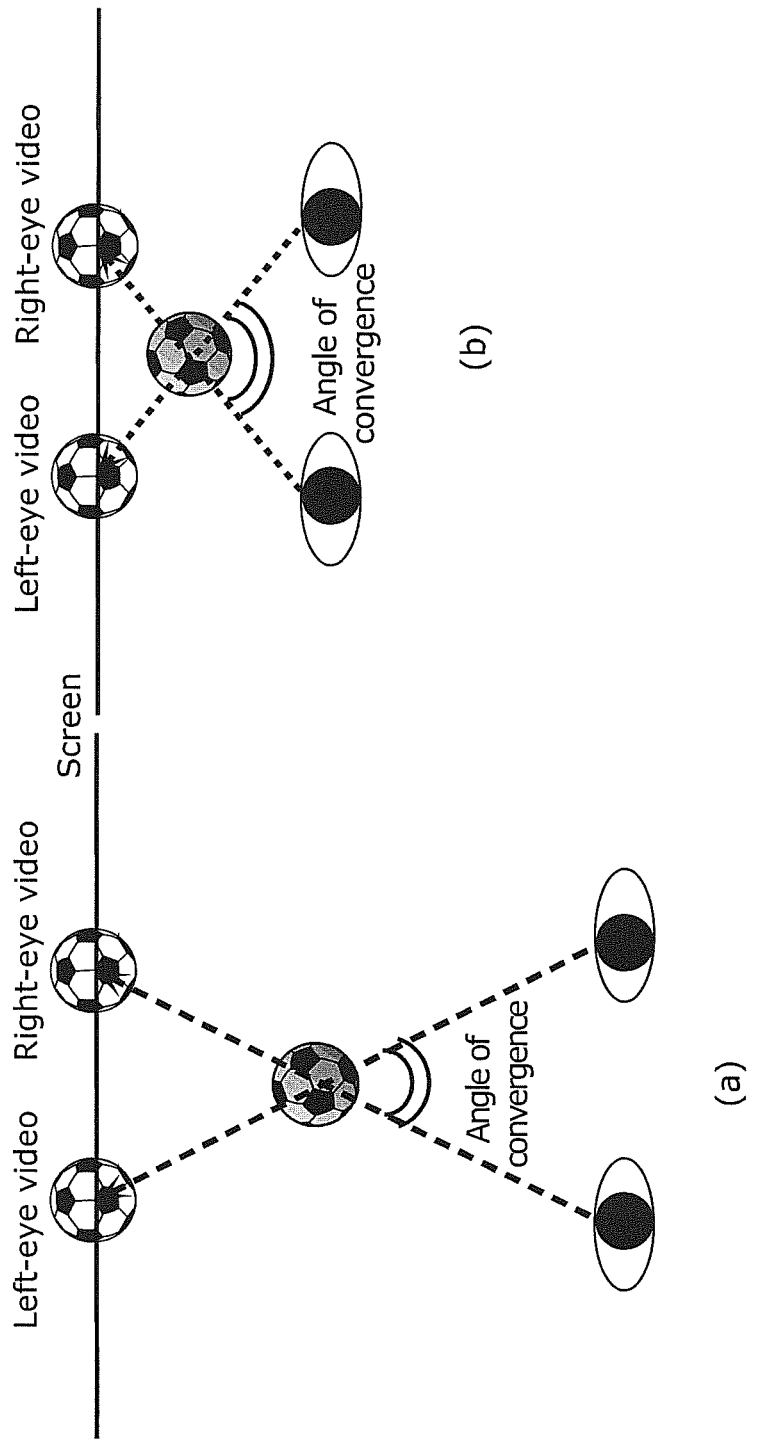
FIG. 10 is a diagram illustrating a difference in angle of convergence, depending on a viewing position of the user.

Here, the convergence amount distribution in the evaluation interval is distribution indicating what amount of convergence is present in the evaluation interval for how long. The ideal convergence amount distribution is the convergence amount distribution assumed by the creator of the stereoscopic video. As the method to determine the ideal convergence amount distribution, the creator of the stereoscopic video may assume a point to be viewed on the screen by the user in the evaluation interval, and calculate an ideal convergence amount when the user looks at the assumed point to calculate the ideal convergence amount distribution. Alternatively, an experiment may be performed in which the same stereoscopic video is shown to a plurality of test viewers to obtain the convergence amount distributions of the test viewers in each evaluation interval at the experiment, and the most frequent convergence amount distribution may be regarded as the ideal convergence amount distribution. It should be noted that in obtaining the ideal distribution using the plurality of test viewers, a test on the convergence performance may be performed on the plurality of test viewers in advance, and the experiment may be performed only on test viewers who can correctly perform the convergence movements. A specific test method is, for example, to measure the amounts of convergence of the test viewer when shown stereoscopic images having various degrees of stereoscopy, and test whether the amounts of convergence are within a predetermined range to calculated values. Likewise, rates of change of the amounts of convergence of the test viewers may be measured when the test viewers are shown a video displaying an object moving at a predetermined rate while the degree of stereoscopy is changing, to test whether the rates of change are within a predetermined range. Meanwhile, as shown in FIG. 10, even in the same stereoscopic video, the amount of convergence is different depending on a distance of the user from the screen (hereinafter, described as "viewing distance"). Thus, when determining the ideal convergence amount distribution, a general viewing position from the TV may be assumed to determine the ideal convergence amount distribution at the assumed position.

The data of the ideal convergence amount distribution stored in the convergence pattern storage unit 105 is stored for each stereoscopic video and each degree of stereoscopy. Hereinafter, the data will be described as "convergence pattern."

Figure 11:
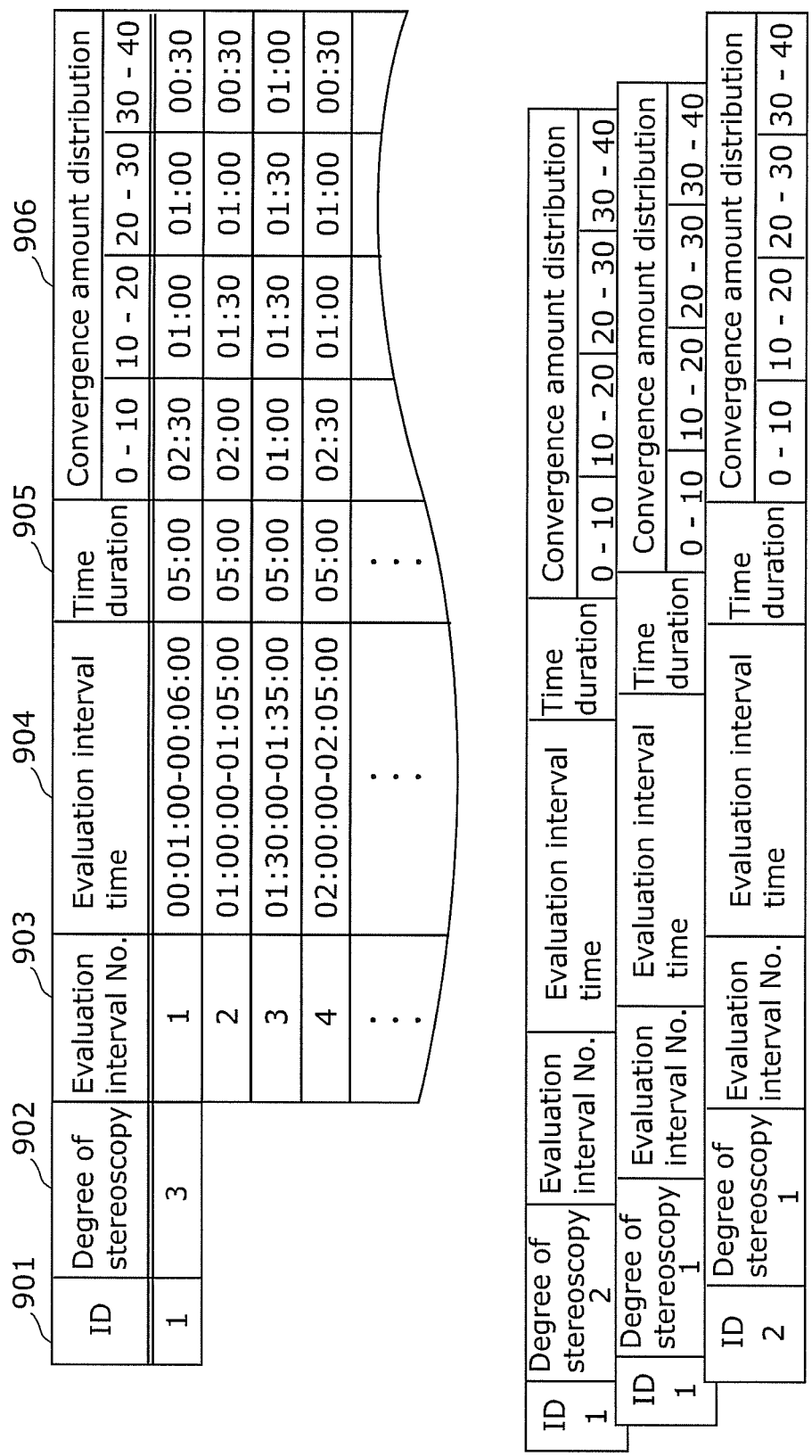
FIG. 11 is a diagram showing an example of data of convergence patterns stored in a convergence pattern storage unit.

An example of the convergence patterns stored in the convergence pattern storage unit 105 is shown in FIG. 11.

In FIG. 11, an item 901 indicates an ID assigned for each stereoscopic video. An item 902 indicates a degree of stereoscopy of the stereoscopic video. The larger the value indicated by the item 902, the greater the degree of stereoscopy of the stereoscopic video when displayed. An item 903 indicates an evaluation interval number. An item 904 indicates an evaluation interval time corresponding to an evaluation interval indicated by the evaluation interval number. The evaluation interval time indicates the start time and end time of the evaluation interval, based on the elapsed time since a playback start time of the stereoscopic video. For example, the start time of the evaluation interval time indicated by the evaluation interval No. 1 in FIG. 11 is one minute after the playback start time of the stereoscopic video, and six minutes thereafter is the end time of the evaluation interval. An item 905 indicates time duration of the evaluation interval. For example, the time duration of the evaluation interval indicated by the evaluation interval No. 1 in FIG. 11 is five minutes. An item 906 indicates the convergence amount distribution. The convergence amount distribution indicates what amounts of convergence are present in a corresponding evaluation interval for how long (total duration in each amount of convergence). In the case of FIG. 11, the convergence amount distribution indicates a total duration of each amount of convergence obtained by dividing, in units of 10 pixels, a difference between the amount of convergence and an amount of convergence in the case where the user looks at an object positioned on the screen. More specifically, items on a column "0-10" in the item 906 are each a total duration of the video in which a difference value between the amount of convergence compared and the amount of convergence in the case where the user looks at an object positioned on the screen is between 0 to 10 pixels. In the case of the evaluation interval No. 1, the total duration is 2 minutes and 30 seconds. Hereinafter, the distribution of amounts of convergence calculated based on the ideal amounts of convergence will be described as "ideal convergence amount distribution".

FIG. 12 shows an example obtained by graphing the convergence amount distribution of the evaluation interval No. 1 in FIG. 11. In step S403, the evaluation interval determination unit 106 acquires information (hereinafter, described as "playing video information") on the stereoscopic video acquired, by the stereoscopic video information acquisition unit 104, from a TV displaying the stereoscopic video or a player playing back the stereoscopic video. Specifically, for example, the evaluation interval determination unit 106 acquires, at 1 second intervals, data which includes information, such as an ID of the stereoscopic video, a current degree of stereoscopy, the elapsed time (hour: minute: second) since the start time of the stereoscopic video, and a total amount of convergence as shown in FIG. 13, for example. The total amount of convergence is an integrated value of the amounts of convergence from the start time of the stereoscopic video to the elapsed time.

The stereoscopic video information acquisition unit 104 also transmits the playing video information to the convergence movement calculation unit 102. Upon reception of the playing video information, the convergence movement calculation unit 102 stores the elapsed time since the start of the stereoscopic video in association with the measured and calculated amount of convergence as shown in an item 1805 in FIG. 14. Date and time of the measurement in an item 1801 represented by "−1" in the item 1805 indicates date and time of the measurement off the evaluation interval. An item 1802 in FIG. 14 indicates an x-coordinate (in pixel units) of the pupil center coordinates of the right eye, an item 1803 in FIG. 14, indicates an x-coordinate (in pixel units) of the pupil center coordinates of the left eye, and an item 1804 in FIG. 14 indicates the amount of convergence. To calculate, as the amount of convergence, reduction of horizontal pupillary distance from the horizontal pupillary distance between the eyes looking on the screen, the horizontal pupillary distance between the eyes looking on the screen is stored as a predetermined value in the convergence movement calculation unit 102. From the measurement result, the convergence movement calculation unit 102 calculates a difference value between the measured value and the predetermined value, and stores the calculated value as the amount of convergence in the convergence movement storage unit 103. Alternatively, a result obtained by measuring the horizontal pupillary distance between the eyes looking at a planar video may be stored as the amount of convergence of the eyes looking on the screen in the convergence movement calculation unit 102 and used.

Upon reception of the playing video information, the evaluation interval determination unit 106 compares between the elapsed time in the received playing video information and the end time of the evaluation interval stored in the convergence pattern storage unit 105. For example, in FIG. 11, the end time of the evaluation interval of the evaluation interval No. 1 is 0 hour 6 minutes 0 second after the start of the stereoscopic video, and thus, when the elapsed time in the received video information is 0 hour 6 minutes 0 second, the evaluation interval determination unit 106 determines that the evaluation interval of the evaluation interval No. 1 has ended.

When the evaluation interval determination unit 106 determines that the elapsed time since the start time of the stereoscopic video acquired from the stereoscopic video information acquisition unit 104 matches the end time of the evaluation interval ("YES" as a result of step S403), the processing proceeds to step 5404 and the evaluation interval determination unit 106 conveys a corresponding evaluation interval number to the movement performance calculation unit 107. On the other hand, if the elapsed time does not match the end time of the evaluation interval ("NO" as a result of step S403), the processing at the time is ended and the processing after step 5401 is repeatedly performed.

Figures 15, 16A:
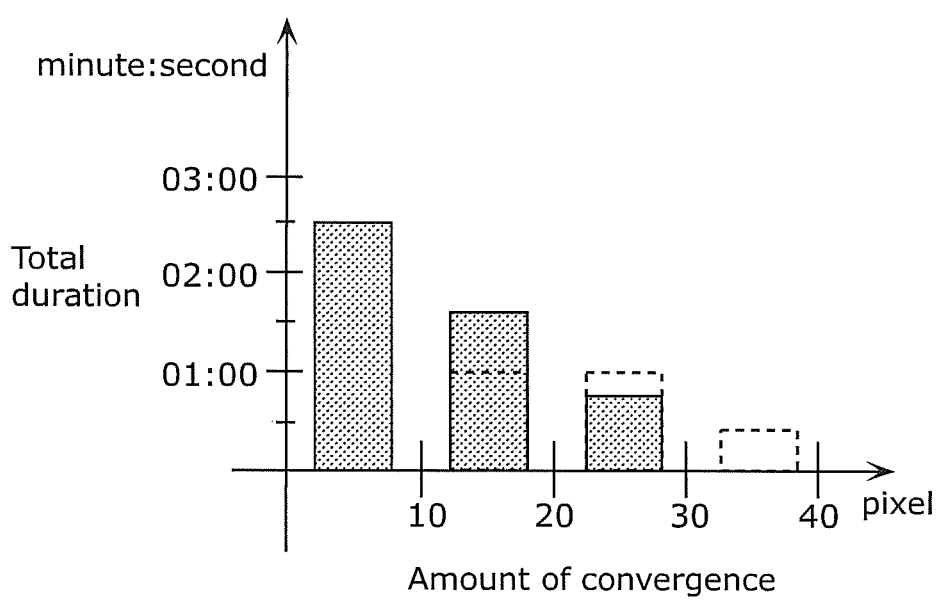
FIG. 15 is a diagram showing an example of a measured convergence amount distribution.
FIG. 16A is a diagram showing an example of the convergence amount distribution stored in the convergence movement storage unit.

In step S404, upon reception of the information that the evaluation interval has ended from the evaluation interval determination unit 106, the movement performance calculation unit 107 first acquires the amounts of convergence in a corresponding evaluation interval from the convergence movement storage unit 103. Next, the movement performance calculation unit 107 calculates the convergence amount distribution of the acquired amounts of convergence, and stores the obtained convergence amount distribution together with the playing video information and the information indicating the evaluation interval in the convergence movement storage unit 103. Specifically, in the case of the evaluation interval No. 1, for example, the movement performance calculation unit 107 acquires amounts of convergence between 1 minute and 6 minutes after the start of the stereoscopic video from the convergence movement storage unit 103. Next, the movement performance calculation unit 107 calculates a segment to which each of the acquired amounts of convergence belong, among segments of the convergence amount distribution where the amounts of convergence are in units of 10 pixels, calculates convergence amount time distribution (hereinafter, the convergence amount time distribution will be described as "measured convergence amount distribution"), based on the number of pieces of data of the amounts of convergence included in each segment. An example of the measured convergence amount distribution stored in the convergence movement storage unit 103 is shown in FIG. 15. An item 1901 indicates an ID of a stereoscopic video currently being viewed. An item 1902 indicates the degree of stereoscopy of the stereoscopic video. An item 1903 indicates the evaluation interval number. An item 1904 indicates the measured convergence amount distribution. If the item 1904 indicates only the measured convergence amount distribution that is calculated based on the measurement result in a timeslot for the evaluation interval No. 1, the calculation result is stored only in an area in which the measured convergence amount distribution of the evaluation interval No. 1 is stored. Once the measured convergence amount distribution has been stored, the movement performance calculation unit 107 conveys a notification indicating the same to the determination unit 108.

Figure 16B:
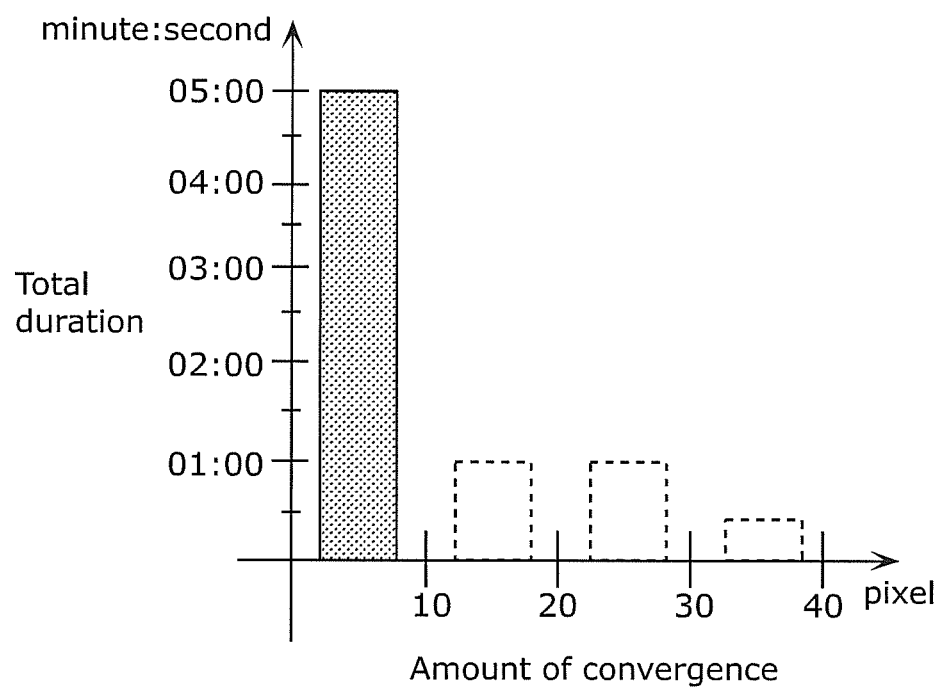
FIG. 16B is a diagram showing an example of the convergence amount distribution stored in the convergence movement storage unit.

In step S405, the determination unit 108 compares the measured convergence amount distribution in the evaluation interval stored in the convergence movement storage unit 103 with the ideal convergence amount distribution in the convergence patterns stored in the convergence pattern storage unit 105 to determine the convergence eye movement performance of the user. Here, the ideal convergence amount distribution to be compared with is the ideal convergence amount distribution in the same evaluation interval as the evaluation interval of the playing video information, among the ideal convergence amount distributions having the same ID and the same degree of stereoscopy as the ID and the degree of stereoscopy of the playing video information on the currently displayed stereoscopic video acquired by the stereoscopic video information acquisition unit 104. As the method to determine the eye movement performance of the user, the determination unit 108 compares the total duration in each amount of convergence with a corresponding total duration in the ideal convergence amount distribution, and determines that the user has poor convergence eye movement performance if the amount of convergence is different from the ideal convergence amount distribution by a predetermined percentage or greater. The specific example will be described with reference to FIG. 16A and FIG. 16B. FIG. 16A and FIG. 16B shows two examples of the convergence amount distributions of the eye movement of the user which is in a certain evaluation interval (the evaluation interval of the evaluation interval No. 1, for example) and stored in the convergence movement storage unit 103. Here, dotted lines in the figures indicate the ideal convergence amount distribution that is shown in FIG. 12 and stored in the convergence pattern storage unit 105, in which total durations of the ideal amounts of convergence in the same evaluation intervals of the measured convergence amounts distribution are shown. In the case of FIG. 16A, when compared with the ideal convergence amount distribution, no amount of convergence is measured in a segment between 30 and 40, and the total duration of the measured amount of convergence in a segment between 20 and 30 is less than the total duration of the ideal amount of convergence in the segment. On the other hand, the total duration of the measured amount of convergence in a segment between 10 and 20 is greater than the total duration of the ideal amount of convergence in the segment. The result determines that the user showing the measured convergence amount distribution as shown in FIG. 16A has no eye movement performance for viewing the stereoscopic video requiring the ideal amount of convergence occurring in the segment between 30 and 40. It is determined that the user also has poor eye movement performance for viewing the stereoscopic video requiring the ideal amount of convergence occurring in the segment between 20 and 30. Likewise, in the case of the user showing the measured convergence amount distribution as in FIG. 16B, it can be seen that no amount of convergence is measured in the segments between 10 and 40 while the amount of convergence in the segment between 0 and 10 is increased. Thus, it is determined that the user has no eye movement performance for viewing the stereoscopic video requiring the ideal amount of convergence occurring in the segments between 10 and 40. It should be noted that, in such a case, detailed convergence amount distributions may be calculated in the segment between 0 and 10. If most values of amounts of convergence in segments between 0 and 10 are zero as a result, it can be seen that the user is unable to perceive the stereoscopic view itself.

As described above, when it is determined that the convergence movement performance required for the amount of convergence in a certain segment is none or poor ("NO" as a result of step S405), the processing proceeds to step 5406. On the other hand, if it is determined that there is no difference between the measured convergence amount distribution of the user and the ideal convergence amount distribution by the predetermined percentage or greater ("YES" as a result of step S405), the processing ends.

In step S406, based on the determination result by the determination unit 108, the stereoscopic degree change unit 109 transmits a request to change the degree of stereoscopy of the currently displayed stereoscopic video, to the TV controlling the degree of stereoscopy of the stereoscopic video or the player playing back the stereoscopic video.

For example, as shown in FIG. 16A, when it is determined that the convergence movement performance required for the segment between 30 and 40 is none, the degree of stereoscopy of the stereoscopic video is changed so that the amount of convergence is 30 pixels maximum. In the case as shown in FIG. 16B, the degree of stereoscopy is changed so that the amount of convergence is 10 pixels maximum. It should be noted that, as mentioned above, when the detailed convergence amount distribution in the segment between 0 and 10 is further examined in FIG. 16B and if most values of the amounts of convergence is zero, the degree of stereoscopy is changed to zero so that the amount of convergence is zero. In other words, the stereoscopic video is changed to the planar video.

Once the degree of stereoscopy of the currently displayed stereoscopic video is changed, it is necessary to change the convergence patterns to be used for the determination of the subsequent convergence eye movement performance of the user. Thus, the stereoscopic degree change unit 109 changes the convergence patterns referred to by the evaluation interval determination unit 106 or the determination unit 108 to convergence patterns suitable for the changed degree of stereoscopy. For example, the convergence patterns having the degree of stereoscopy of 3 which includes the amounts of convergence in the segment range between 30 and 40 as shown in FIG. 11 are changed to convergence patterns having the degree of stereoscopy of which includes the amounts of convergence up to 30 pixels as shown in FIG. 17.

As described above, the convergence performance determination device according to the present embodiment calculates the amounts of convergence of the eyes of a user perceiving the stereoscopic view, based on the eye information of the user viewing the stereoscopic video, and compares the convergence amount distribution with the ideal convergence amount distribution in the evaluation interval, thereby determining the convergence eye movement performance of the user. Thus, the convergence movement performance of the user viewing the stereoscopic video can be determined in each degree of stereoscopy and, based on the result, the degree of stereoscopy of the stereoscopic video can be changed to a degree of stereoscopy suitable for the user. As such, by changing the degree of stereoscopy based on the determination result, the stereoscopic video having the degree of stereoscopy suitable for the user can be presented to the user by changing the degree of stereoscopy by one step. Thus, a stereoscopic video making the user feel low fatigue and low sense of discomfort can be presented to the user.

As described above, while the convergence performance determination device according to the exemplary embodiment is described, the present disclosure is not limited to the exemplary embodiment.

Figure 19:
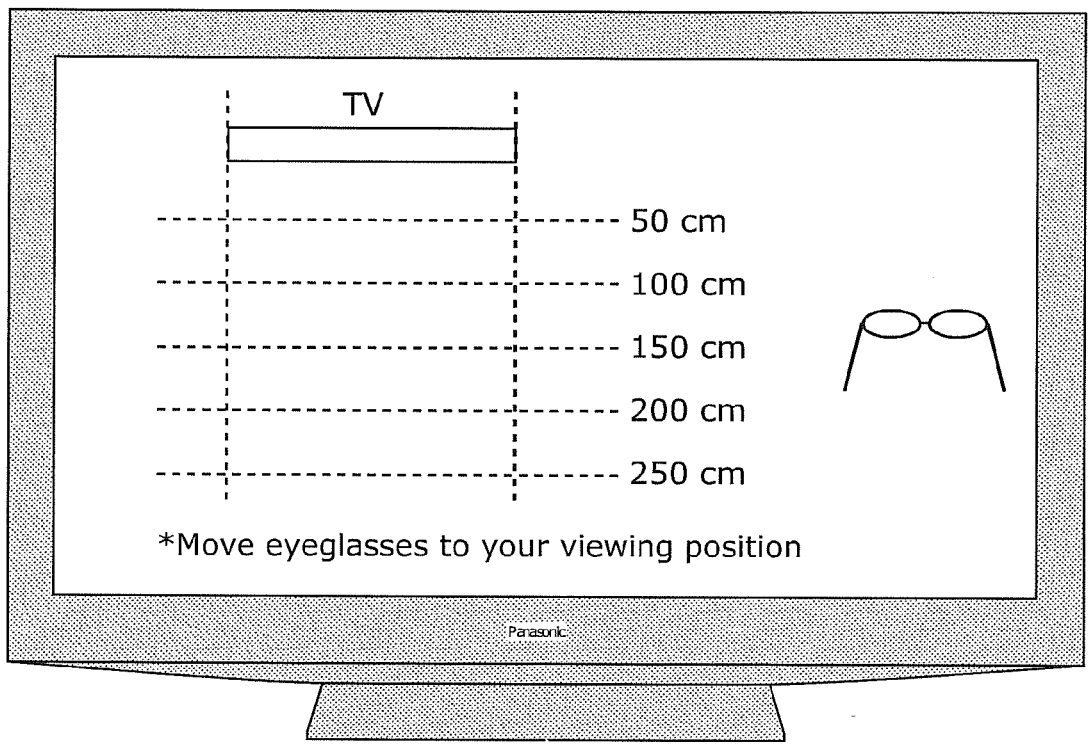
FIG. 19 is a diagram illustrating a method of setting the viewing position.

For example, while the convergence patterns are generated in the above embodiment assuming a general viewing position from a TV, the convergence patterns may be generated for different viewing distances as shown in FIG. 18 (for example, every 50 cm). When a user sets a viewing position (the viewing distance), for example, on a display screen as shown in FIG. 19, convergence patterns that have the most similar viewing distance to the set viewing distance are selected and used for the determination of the convergence movement performance. This allows accurate comparison between the selected convergence patterns and actual values of the amounts of convergence. A functional configuration of the convergence performance determination device in this case is shown in a block diagram of FIG. 20. The convergence performance determination device shown in FIG. 20 is different from that in FIG. 3 in that the convergence performance determination device in FIG. 20 additionally includes a viewing distance input unit 3101 which receives a viewing distance from a user.

In the above embodiment, the convergence eye movement performance of the user is determined by comparing the measured convergence amount distribution with the ideal convergence amount distribution in the evaluation interval. Here, the convergence movement performance can be determined at high accuracy due to the fact that a location from which the user is actually viewing the stereoscopic video in the evaluation interval matches the location from which the user is viewing the stereoscopic video that is assumed in generating the convergence pattern.

This is a case where, for example, there are two people A and B having different depths on the screen. If, despite that the test viewer is looking at the person A, the amounts of convergence movement in the case where the test viewer is looking at the person B are recorded as the convergence patterns, the ideal convergence amount distribution and the measured convergence amount distribution are different although the user is able to perceive the person A in a stereoscopic manner. Due to this, the determination unit 108 ends up determining that there is a problem in the convergence eye movement performance of the user. To accurately determine the convergence eye movement performance of the user, it is necessary to set the evaluation interval of the convergence pattern highly likely to be the evaluation interval to which the measured convergence amount distribution belongs.

Thus, a block diagram showing a functional configuration of a convergence pattern generation device which generates the convergence patterns of a certain stereoscopic video in the above embodiment is shown in FIG. 21. FIG. 22 is a flowchart illustrating operation of the convergence pattern generation device.

The convergence pattern generation device includes an eye movement acquisition unit 2401, a convergence movement calculation unit 2402, a convergence movement storage unit 2403, an evaluation interval determination unit 2404, a convergence pattern generation unit 2405, and the convergence pattern storage unit 105.

In step S2501, first, a test stereoscopic video is shown to a plurality of test viewers, and a predetermined number of test viewers only who can correctly perform the convergence movement are extracted. This extraction process may use the convergence performance determination device shown in FIG. 3 to calculate a difference between the measured convergence amount distribution and the ideal convergence amount distribution, and extract the predetermined number of test viewers who has small differences between the measured convergence amount distribution and the ideal convergence amount distribution. A stereoscopic video the convergence patterns for which are to be generated is shown to the extracted plurality of test viewers, and the eye movements then are measured by the eye movement acquisition unit 2401.

Figure 23:
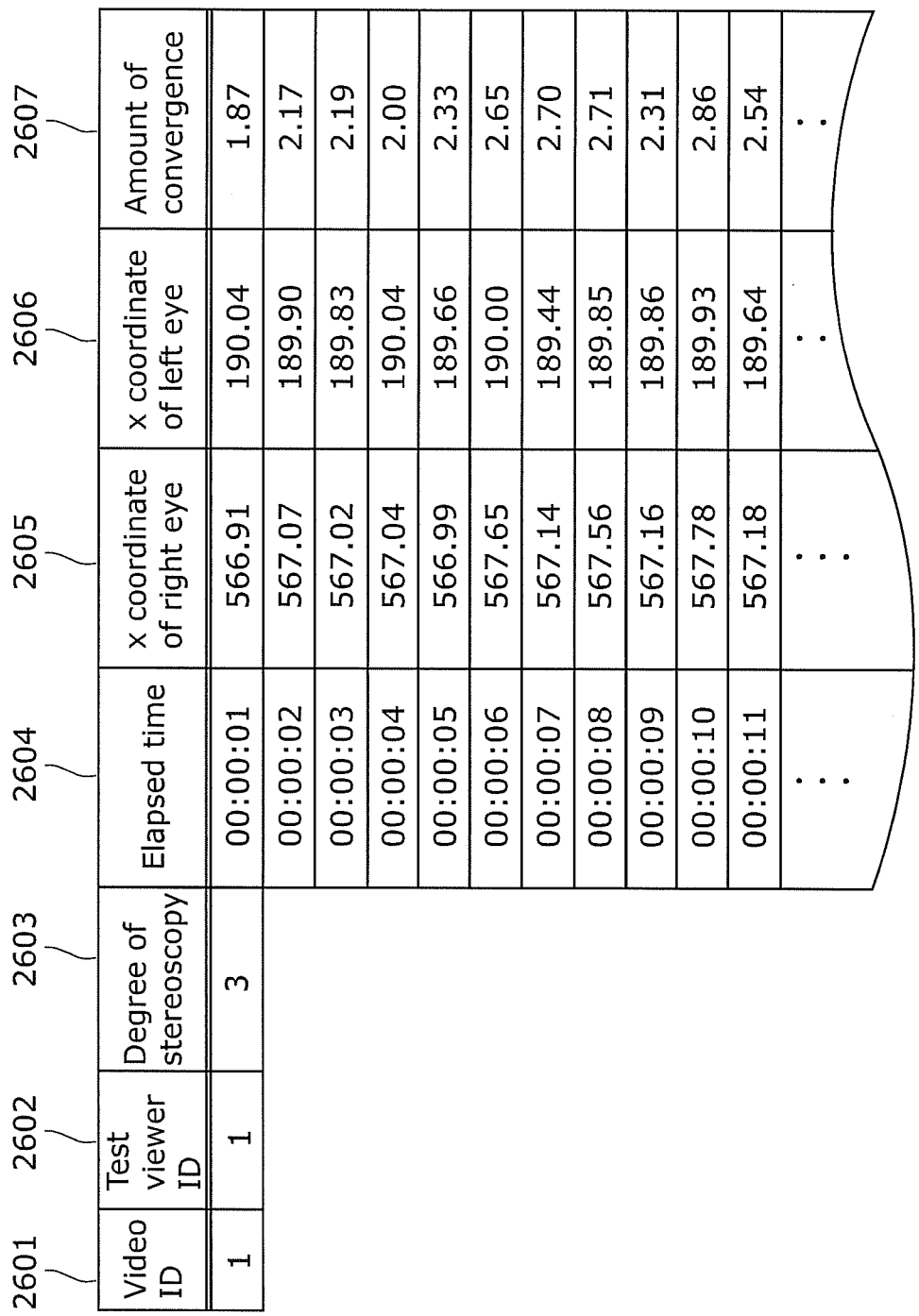
FIG. 23 is a diagram showing an example of data of the convergence movements of one viewer stored in the convergence movement storage unit.

In step S2502, the convergence movement calculation unit 2402 calculates the amount of convergence movement, based on the measured eye movement, and stores the obtained amount of convergence movement in the convergence movement storage unit 2403. Specifically, a time-series data of the amounts of convergence is calculated and recorded as the amount of convergence movement. Here, as with the above embodiment, the amount of convergence is defined, for example, as reduction of the horizontal pupillary distance between the eyes based on the horizontal pupillary distance between the eyes looking at a non-stereoscopic video on the screen. FIG. 23 shows an example of the measurement result of a test viewer stored in the convergence movement storage unit 2403. An item 2601 indicates an ID of a target stereoscopic video. An item 2602 indicates an ID of the test viewer. An item 2603 indicates a degree of stereoscopy of the target stereoscopic video. An item 2604 indicates the elapsed time since the start of the target stereoscopic video. An item 2605, an item 2606, and an item 2607 indicate, as with the embodiment, an x coordinate of the right eye, an x coordinate of the left eye, and an amount of convergence, respectively. The amount of convergence is obtained by subtracting, from a difference value between the x coordinates of the left and right eyes, a difference value between the x coordinates of the left and right eyes looking at an object positioned on the screen.

In step S2503, the evaluation interval determination unit 2404 calculates an average value and a variance value of the time-series data, calculated in step S2502, of the amounts of convergence of the plurality of test viewers, and stores the results in the convergence movement storage unit 103. An example of the stored results of the average value and the variance value is shown in FIG. 24. An item 2701 indicates an ID of the target stereoscopic video. An item 2702 indicates the degree of stereoscopy of the target stereoscopic video. An item 2703 indicates the elapsed time since the start of the target stereoscopic video. An item 2704 indicates the amounts of convergence of each test viewer. An item 2705 and an item 2706 indicate the average value and the variance value, respectively, of the amounts of convergence indicated in the item 2704.

In step S2504, the evaluation interval determination unit 2404 determines the evaluation intervals, based on the variance value, calculated and stored in step S2503, of the amounts of convergence of the test viewers for each elapsed time since the start time of the stereoscopic video. Here, since the test viewers are all able to correctly view the stereoscopic video in the stereoscopic manner, the evaluation interval is determined based on a basic idea that the amounts of convergence of the test viewers in the same elapsed time are different due to a fact that the test viewers look at different positions in the stereoscopic video. Specifically, the first evaluation interval is determined by an interval in which the variance value indicated in the item 2706 is less than or equal to a predetermined value for a predetermined time or longer, and the second and later evaluation intervals are determined by an interval in which the variance value indicated in the item 2706 is less than or equal to the predetermined value for the predetermined time or longer and which has elapsed since the previous evaluation interval for a predetermined time or longer. More specifically, the evaluation interval is determined by an interval in which the variance value remains 0.05 or below for five minutes and which has elapsed since the previous evaluation interval for 30 minutes or longer.

The evaluation interval determination unit 2404 stores information on the evaluation intervals determined as described above in the convergence movement storage unit 2403. An example of the information on the evaluation intervals to be stored is shown in FIG. 25. An item 2801 indicates an ID of the target stereoscopic video. An item 2802 indicates the degree of stereoscopy of the target stereoscopic video. An item 2803 indicates an evaluation interval number. An item 2804 and an item 2805 indicate the evaluation interval time (the start time and the end time) and the time duration, respectively, which correspond to the evaluation interval number indicated in the item 2803. The start time and end time of the evaluation interval are represented by the elapsed time since the start of the stereoscopic video.

In step S2505, the convergence pattern generation unit 2405 calculates the distribution of the average values of the amounts of convergence of the plurality of test viewers in each evaluation interval, based on the information on each evaluation interval stored in the convergence movement storage unit 2403 and average values of the amounts of convergence of the plurality of test viewers, generates convergence patterns in a format, for example, as shown in FIG. 11 together with the information on the evaluation intervals, and stores the generated convergence patterns in the convergence pattern storage unit 105.

(Modification 1)

In the above embodiment, the convergence amount distribution of the users in the evaluation interval is compared with the convergence patterns. In other words, the distribution indicating what amount of convergence occurs for how long in the evaluation interval is compared with the ideal distribution, thereby determining the convergence eye movement performance of the user.

In the present modification, as a parameter for use to determine the convergence eye movement performance of the user, a convergence rate distribution is used instead of on the convergence amount distribution. Most of the processing of the present modification is the same as that of the embodiment, and thus only the difference will be described below.

To determine the convergence eye movement performance of the user, based on the convergence rate distribution instead of the convergence amount distribution, the convergence patterns indicating an ideal convergence rate distribution is stored in the convergence pattern storage unit 105. The convergence rate distribution is calculated as follows. In other words, the ideal amounts of convergence as shown in (a) of FIG. 26 are differentiated to calculate the convergence rates, which are rates of change in amount of convergence as shown in (b) of FIG. 26. Using the convergence rates, the ideal convergence rate distribution indicating how long each convergence rate is present in the evaluation interval is calculated. FIG. 27 shows an example of the convergence patterns indicating the ideal convergence rate distribution. It should be noted that while in FIG. 27, an example is shown in which absolute values of the convergence rates are calculated and the distribution of the absolute values is stored, the convergence rate distribution that includes negative rates may be stored. An item 2201, an item 2202, an item 2203, an item 2204, and an item 2205 are the same as the item 901, the item 902, the item 903, the item 904, and the item 905, respectively, in the case of the convergence patterns shown in FIG. 11, and thus the description will not be repeated. An item 2206 indicates the convergence rate distribution. The convergence rate distribution indicates the magnitude of each convergence rate present in a corresponding evaluation interval for how long (total duration in each convergence rate). In the case of FIG. 27, the convergence rate distribution indicates a total duration of the convergence rate divided in units of 5 pixels/second. More specifically, items on a column "0-5" in the item 2206 are each a total duration of the video having the convergence rates between 0 to 5 pixels/second. In the case of the evaluation interval No. 1, the total duration is 2 minutes and 30 seconds.

As with the above embodiment, the movement performance calculation unit 107 calculates a convergence rate distribution instead of the convergence amount distribution, based on the calculation result of the convergence movement stored in the convergence movement storage unit 103, and stores the result in the convergence movement storage unit 103 in a format, for example, as shown in FIG. 28. An item 2301, an item 2302, and an item 2303 are the same as the item 1901, the item 1902, and the item 1903, respectively, of the measured convergence amount distribution shown in FIG. 15, and thus, the description will not be repeated. An item 2304 indicates a measured convergence rate distribution. Given that only the measured convergence rate distribution calculated from the measurement result in a timeslot for the evaluation interval No. 1 is calculated, the calculation result is stored only in an area in which the measured convergence rate distribution of the evaluation interval No. 1 is stored. After the measured convergence rate distribution is stored, the movement performance calculation unit 107 conveys a notification indicating the same to the determination unit 108.

The determination unit 108 compares the convergence rate distribution of the eyes of the user with the convergence rate distribution of the convergence patterns in the same evaluation interval to determine the convergence eye movement performance of the user. In the distribution of the convergence eye movements of the user, if the distribution of the convergence eye movements having high rates is smaller than the distribution of the convergence patterns, it is determined that the user is unable to follow the change in the degree of stereoscopy in the stereoscopic video.

When the determination unit 108 determines that the user is unable to follow the change in a certain degree of stereoscopy in the convergence eye movement performance of the user, the stereoscopic degree change unit 109 reduces the degree of stereoscopy of the currently displayed stereoscopic video so that the displayed stereoscopic video has a degree of stereoscopy which can be followed by the user.

As described above, the convergence performance determination device according to the present modification calculates the convergence rates of the eyes of the user perceiving the stereoscopic view, from the eye information of the user viewing the stereoscopic video, and compares the convergence rate distribution with the ideal convergence rate distribution in the evaluation interval, thereby determining the convergence eye movement performance of the user. Thus, the convergence movement performance of the user viewing the stereoscopic video can be determined in each degree of stereoscopy and, based on the result, the degree of stereoscopy of the stereoscopic video can be changed to a degree of stereoscopy suitable for the user. As such, by changing the degree of stereoscopy based on the determination result, the stereoscopic video having the degree of stereoscopy suitable for the user can be presented to the user by changing the degree of stereoscopy by one step. Thus, a stereoscopic video making the user feel low fatigue and low sense of discomfort can be presented to the user.

(Modification 2)

In the above embodiment, the convergence eye movement performance of the user is determined by comparing the convergence amount distribution of the user with the convergence patterns in the evaluation interval.

In the present modification, a method will be described in which, instead of the ideal convergence pattern distribution, only the evaluation intervals and information indicating whether a value of each amount of convergence is present in an ideal state are stored in the convergence pattern storage unit 105 and the convergence movement performance is determined.

Figure 29:
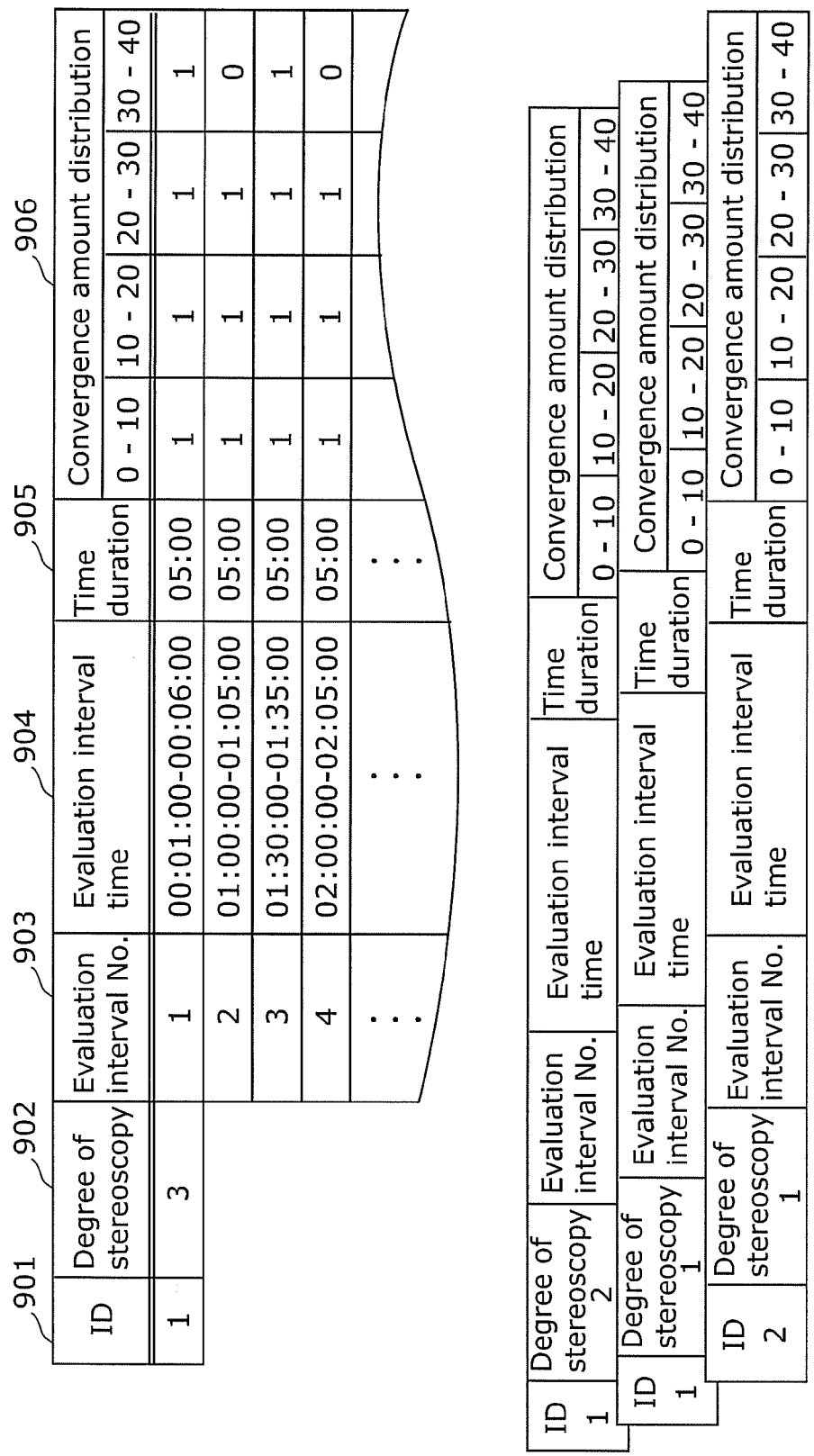
FIG. 29 is a diagram showing an example of the convergence patterns stored in the convergence pattern storage unit according a modification 2 of the exemplary embodiment.

An example of the convergence patterns stored in the convergence pattern storage unit 105 in the present modification is shown in FIG. 29. FIG. 29 is different from FIG. 11 in that binary either 0 or 1 is stored in the item 906 in FIG. 29, unlike as in the above embodiment in which the total duration in each convergence amount range is stored in the item 906. The value 1 indicates that there is the amount of convergence that falls within the convergence amount range, and the value 0 indicates that there is no amount of convergence that falls within the convergence amount range.

As with the above embodiment, the movement performance calculation unit 107 calculates and stores the measured convergence amount distribution in the evaluation interval in the convergence movement storage unit 103. The determination unit 108 compares the calculation result with the ideal convergence amount distribution stored in the convergence pattern storage unit 105. If there is no measured amount of convergence that falls within the convergence amount range in which the value in the ideal convergence amount distribution is 1, the stereoscopic degree change unit 109 changes the degree of stereoscopy of the stereoscopic video to a degree of stereoscopy that causes only a small amount of convergence that falls within the convergence amount range in which no amount of convergence is present.

The present modification allows reduction in size of the convergence patterns stored in the convergence pattern storage unit 105 and also reduction in complexity required in determining the convergence movement performance.

(Modification 3)

In the above embodiment, the convergence eye movement performance of the user is determined by comparing the measured convergence amount distribution with the ideal convergence amount distribution in the evaluation interval.

In the present modification, the convergence eye movement performance of the user is determined by comparing between the measured convergence amount distributions in the evaluation intervals having different timeslots, without storing the ideal convergence amount distribution as the convergence patterns.

A configuration of the convergence performance determination device according to the present modification is same as that shown in FIG. 3.

An example of the convergence patterns stored in the convergence pattern storage unit 105 in the present modification is shown in FIG. 30. An item 3201 indicates an ID of the stereoscopic video. An item 3202 indicates an evaluation interval number. An item 3203 indicates an evaluation interval time corresponding to an evaluation interval denoted by the evaluation interval number. An item 3204 indicates time duration of the evaluation interval. Here, the present modification is different from the above embodiment in that the ideal convergence amount distributions in all the evaluation intervals in the present modification are equal to each other. For example, it is assumed that the ideal convergence amount distribution in the present modification is as shown in FIG. 31. Thus, the convergence patterns shown in FIG. 30 do not include the ideal convergence amount distribution. Moreover, since the ideal convergence amount distributions in all the evaluation intervals are equal to each other, irrespective of the degree of stereoscopy, the convergence patterns for each degree of stereoscopy are also not stored.

The processing performed by the convergence performance determination device according to the present modification is the same as the processing performed by the convergence performance determination device according to the above embodiment shown in FIG. 4 except that the processing after step S404 is different. Thus, the difference from the above embodiment will be described below.

In step S404, upon reception of information that the evaluation interval has ended from the evaluation interval determination unit 106, the movement performance calculation unit 107 calculates the measured convergence amount distribution in the ended evaluation interval, and stores the measured convergence amount distribution as shown in FIG. 15 in the convergence movement storage unit 103. Here, if the ended evaluation interval is the first evaluation interval, the determination unit 108 does not determine the convergence eye movement performance of the user. In other words, the processing proceeds from step S404 to End.

On the other hand, if the ended evaluation interval is not the first evaluation interval, the processing proceeds to step S405, the determination unit 108 compares between the measured convergence amount distributions in the ended evaluation interval and the evaluation interval one previous to the ended evaluation interval, to determine whether the amount of convergence in each convergence amount range decreases by a predetermined percentage or greater. Here, if there is no reduction in convergence amount by the predetermined percentage or greater in any convergence amount range, the processing proceeds to End. On the other hand, there is the reduction in convergence amount by the predetermined percentage or greater in a certain convergence amount range, the processing proceeds to step S406. In step S406, the stereoscopic degree change unit 109 sends a request to change the degree of stereoscopy so that the degree of stereoscopy has no convergence amount range in which there is the reduction in convergence amount by the predetermined percentage or greater, to the TV controlling the degree of stereoscopy of the stereoscopic video or the player playing back the stereoscopic video.

According to the determination method of the present modification, temporal deterioration in convergence movement performance due to the user when viewing the stereoscopic video is detectable, provided that the original convergence movement performance of the user cannot be determined. However, implementation of the determination method of the present modification allows reduction in size of the convergence patterns stored in the convergence pattern storage unit 105.

Essential components of the present disclosure, among the components of the convergence performance determination device shown in FIG. 3, is the eye information acquisition unit 101, the convergence movement calculation unit 102, and the determination unit 108. It is desirable but may not be necessary that the convergence performance determination device includes the other components. FIG. 32 is a block diagram showing a functional configuration of the convergence performance determination device which includes the essential components of the present disclosure. The convergence performance determination device is a convergence performance determination device for determining convergence eye movement performance of a user, based on a state of the eyes of the user when viewing a stereoscopic video, the convergence performance determination device including: an eye information acquisition unit 101 configured to acquire eye information which is information on eye movements of a user when viewing a stereoscopic video; a convergence movement calculation unit 102 configured to calculate amounts of convergence movement each indicating a degree of a convergence eye movement of the user, based on the eye information acquired by the eye information acquisition unit 101; and a determination unit 108 configured to determine convergence eye movement performance of the user by comparing between distribution data indicating a distribution of the amounts of convergence movement calculated by the convergence movement calculation unit 102 in an evaluation interval which is a predetermined playback time interval of the stereoscopic video being viewed by the user and distribution data indicating a distribution of the amounts of convergence movement determined in accordance with depth information on the stereoscopic video in the evaluation interval.

It should be noted that each device described above may be configured as a computer system which includes, specifically, a microprocessor, a ROM, a RAM, a hard disk drive, a display unit, a keyboard, a mouse, and the like. A computer program is stored in the RAM or the hard disk drive. The function of each device is performed by the microprocessor operating in accordance with the computer program. Here, the computer program includes a combination of a plurality of instruction codes for giving instructions to the computer to perform predetermined functions.

Furthermore, part or the whole of the components included in each of the devices described above may be configured with one system LSI (Large Scale Integration). The system LSI is a super multi-function LSI manufactured by integrating a plurality of components on one chip, and is, specifically, a computer system which includes a microprocessor, a ROM, a RAM, or the like. The computer program is stored in the RAM. The system LSI performs its functionality by the microprocessor operating in accordance with the computer program.

Furthermore, part or the whole of the components included in each of the devices described above may be configured with an IC card or a single module detachable to each device. The IC card or the module is a computer system which includes a microprocessor, a ROM, a RAM, or the like. The IC card or the module may include the super multi-function LSI described above. The IC card or the module performs its functionality by the microprocessor operating in accordance with the computer program. The IC card or the module may be of tamper-resistant.

Moreover, the present disclosure may be implemented as the methods described above. Moreover, the present disclosure may be achieved as a computer program implementing such methods via a computer, or may be implemented as digital signals including the computer program.

In other words, the computer program causes the computer to execute processes included in a convergence performance determination method. The convergence performance determination method includes: acquiring eye information which is information on eye movements of a user when viewing a stereoscopic video; calculating amounts of convergence movement each indicating a degree of the convergence eye movement of the user, based on the eye information acquired in the eye information acquisition; and determining convergence eye movement performance of the user by comparing distribution data indicating a distribution of the amounts of convergence movement calculated by the calculation in an evaluation interval which is a predetermined playback time interval of the stereoscopic video being viewed by the user with distribution data indicating a distribution of the amounts of convergence movement determined in accordance with depth information on the stereoscopic video in the evaluation interval.

Furthermore, the present disclosure may be achieved as a non-transitory computer-readable recording medium having recorded therein the computer program or the digital signals, such as a flexible disk, a hard disk, CD-ROM, MO, DVD, DVD-ROM, DVD-RAM, BD (Blu-ray Disc (registered trademark)), and a semiconductor memory. Moreover, the present disclosure may be implemented as the digital signals recorded in such the non-transitory recording medium.

Moreover, the present disclosure may be achieved as transmitting the computer program or the digital signals via an electric communication line, a wireless or wired communication line, a network represented by the Internet, data broadcast, or the like.

Moreover, the present disclosure may be achieved as a computer system which includes a microprocessor and a memory, the memory may store therein the computer program, and the microprocessor operates in accordance with the computer program.

Moreover, by transferring the program or the digital signals recorded in the non-transitory recording medium, or transferring the program or the digital signals via the network or the like, the program or the digital signals may be executed in other independent computer system.

While only one or more exemplary embodiments of the present disclosure have been described based on the exemplary embodiment, the present disclosure is not limited to the exemplary embodiment. Various modifications to the present embodiments that may be conceived by those skilled in the art and combinations of components of different embodiments are intended to be included within the scope of the one or more exemplary embodiments, without departing from the spirit of the one or more exemplary embodiments.

The herein disclosed subject matter is to be considered descriptive and illustrative only, and the appended Claims are of a scope intended to cover and encompass not only the particular embodiments) disclosed, but also equivalent structures, methods, and/or uses.

Industrial Applicability

A convergence performance determination device according to one or more exemplary embodiments herein enables to present a stereoscopic video having a degree of stereoscopy suitable for each of users having various convergence movement performances. One or more exemplary embodiments disclosed herein are applicable to a large number of stereoscopic video devices in which the degree of stereoscopy is changeable. Thus one or more exemplary embodiments disclosed herein have high industrial applicability.

The invention claimed is:

1. A convergence performance determination device comprising:
   processing circuitry; and
   a non-transitory memory having executable instructions stored therein, which when executed by the processor, cause the processing circuitry to perform:
      acquiring eye information which is information on eye movements of a user when viewing a stereoscopic video;
      calculating, as calculated amounts of convergence movement, amounts of convergence movement each indicating an amount of a convergence eye movement of the user, based on the acquired eye information; and
      determining, for an evaluation interval which is a predetermined playback time interval of the stereoscopic video being viewed by the user, convergence eye movement performance of the user by comparing, on a segment-by-segment basis, (i) a plurality of segments included in a distribution of predetermined amounts of convergence movement determined in accordance with depth information on the stereoscopic video with (ii) a plurality of segments included in a distribution of the calculated amounts of convergence movement,
   wherein each of the plurality of segments included in the distribution of the predetermined amounts of convergence movement indicates a total duration during which a range of the predetermined amounts of convergence movement is present, and
   wherein each of the plurality of segments included in the distribution of the calculated amounts of convergence movement indicates a total duration during which a range of the calculated amounts of convergence movement is present.

2. The convergence performance determination device according to claim 1,
   wherein the convergence eye movement performance of the user is determined to be inadequate for viewing the stereoscopic video in a segment, which is included in the plurality of segments included in the distribution of the predetermined amounts of convergence movement, when (i) the total duration during which the range of the predetermined amounts of convergence movement is present in the segment is smaller than (ii) the total duration during which the range of the calculated amounts of convergence movement is present in a corresponding segment in the plurality of segments included in the distribution of the calculated amounts of convergence movement.

3. The convergence performance determination device according to claim 1,
   wherein the evaluation interval is the playback time interval of the stereoscopic video when variance values of the amounts of convergence movement of a plurality of test viewers viewing the stereoscopic video are continuously less than or equal to a predetermined value for a predetermined time or longer.

4. The convergence performance determination device according to claim 1,
   wherein the calculated amounts of convergence movement and the predetermined amounts of convergence movement are amounts of convergence indicating values corresponding to pupillary distances between the left eye and the right eye of the user.

5. The convergence performance determination device according to claim 1,
wherein the calculated amounts of convergence movement and the predetermined amounts of convergence movement are convergence rates indicating time variations in amount of convergence indicating values corresponding to pupillary distances between the left eye and the right eye of the user.

6. The convergence performance determination device according to claim 1,
wherein the executable instructions further cause the processing circuitry to perform
reducing amounts of convergence included in the stereoscopic video when the convergence eye movement performance of the user is determined to be inadequate for viewing the stereoscopic video.

7. A convergence performance determination method comprising:
acquiring eye information which is information on eye movements of a user when viewing a stereoscopic video;
calculating, as calculated amounts of convergence movement, amounts of convergence movement each indicating an amount of the convergence eye movement of the user, based on the acquired eye information; and
determining, for an evaluation interval which is a predetermined playback time interval of the stereoscopic video being viewed by the user, convergence eye movement performance of the user by comparing, on a segment-by-segment basis, (i) a plurality of segments included in a distribution of predetermined amounts of convergence movement determined in accordance with depth information on the stereoscopic video with (ii) a plurality of segments included in a distribution of the calculated amounts of convergence movement,
wherein each of the plurality of segments included in the distribution of the predetermined amounts of convergence movement indicates a total duration during which a range of the predetermined amounts of convergence movement is present, and
wherein each of the plurality of segments included in the distribution of the calculated amounts of convergence movement indicates a total duration during a which a range of the calculated amounts of convergence movement is present.

8. A non-transitory computer-readable recording medium having stored therein a program for causing a computer to execute a convergence performance determination method comprising:
acquiring eye information which is information on eye movements of a user when viewing a stereoscopic video;
calculating, as calculated amounts of convergence movement, amounts of convergence movement each indicating an amount of the convergence eye movement of the user, based on the acquired eye information; and
determining, for an evaluation interval which is a predetermined playback time interval of the stereoscopic video being viewed by the user, convergence eye movement performance of the user by comparing, on a segment-by-segment basis, (i) a plurality of segments included in a distribution of predetermined amounts of convergence movement determined in accordance with depth information on the stereoscopic video with (ii) a plurality of segments included in a distribution of the calculated amounts of convergence movement,
wherein each of the plurality of segments included in the distribution of the predetermined amounts of convergence movement indicates a total duration during which a range of the predetermined amounts of convergence movement is present, and
wherein each of the plurality of segments included in the distribution of the calculated amounts of convergence movement indicates a total duration during a which a range of the calculated amounts of convergence movement is present.

* * * * *